US009393217B2

(12) United States Patent
Hammond et al.

(10) Patent No.: US 9,393,217 B2
(45) Date of Patent: Jul. 19, 2016

(54) SELF ASSEMBLED FILMS FOR PROTEIN AND DRUG DELIVERY APPLICATIONS

(71) Applicant: Massachusetts Institute of Technology, Cambridge, MA (US)

(72) Inventors: Paula T. Hammond, Newton, MA (US); Mara L. Macdonald, Arvada, CO (US)

(73) Assignee: Massachusetts Institute of Technology, Cambridge, MA (US)

( * ) Notice: Subject to any disclaimer, the term of this patent is extended or adjusted under 35 U.S.C. 154(b) by 7 days.

(21) Appl. No.: 14/511,589

(22) Filed: Oct. 10, 2014

(65) Prior Publication Data

US 2015/0086599 A1 Mar. 26, 2015

Related U.S. Application Data

(62) Division of application No. 12/139,151, filed on Jun. 13, 2008.

(60) Provisional application No. 60/943,983, filed on Jun. 14, 2007.

(51) Int. Cl.
| | |
|---|---|
| A61K 9/70 | (2006.01) |
| A61L 27/34 | (2006.01) |
| A61L 27/54 | (2006.01) |
| A61L 27/58 | (2006.01) |
| A61L 31/10 | (2006.01) |
| A61L 31/14 | (2006.01) |
| A61L 33/08 | (2006.01) |
| B82Y 30/00 | (2011.01) |
| A61K 31/726 | (2006.01) |
| A61K 31/727 | (2006.01) |
| A61K 38/18 | (2006.01) |
| A61L 31/16 | (2006.01) |
| A61L 33/00 | (2006.01) |
| A61K 38/00 | (2006.01) |

(52) U.S. Cl.
CPC .............. *A61K 9/7007* (2013.01); *A61K 31/726* (2013.01); *A61K 31/727* (2013.01); *A61K 38/1825* (2013.01); *A61K 38/1866* (2013.01); *A61K 38/1875* (2013.01); *A61L 27/34* (2013.01); *A61L 27/54* (2013.01); *A61L 27/58* (2013.01); *A61L 31/10* (2013.01); *A61L 31/148* (2013.01); *A61L 31/16* (2013.01); *A61L 33/0011* (2013.01); *A61L 33/08* (2013.01); *B82Y 30/00* (2013.01); *A61K 38/00* (2013.01); *A61L 2300/252* (2013.01); *A61L 2300/42* (2013.01); *A61L 2300/604* (2013.01); *A61L 2300/608* (2013.01); *A61L 2420/02* (2013.01); *A61L 2420/08* (2013.01); *Y10T 428/31768* (2015.04)

(58) Field of Classification Search
CPC ............ A61K 9/7007; A61K 38/1866; A61K 38/1875; A61L 27/58; A61L 27/54; A61L 2420/08

See application file for complete search history.

(56) References Cited

U.S. PATENT DOCUMENTS

| | | | |
|---|---|---|---|
| 3,266,987 | A | 8/1966 | Crowley et al. |
| 3,710,795 | A | 1/1973 | Higuchi et al. |
| 3,962,414 | A | 6/1976 | Michaels |
| 4,191,811 | A | 3/1980 | Hodgdon |
| 4,250,029 | A | 2/1981 | Kiser et al. |
| 4,460,563 | A | 7/1984 | Calanchi |
| 4,638,045 | A | 1/1987 | Kohn |
| 4,794,000 | A | 12/1988 | Ecanow |
| 4,806,621 | A | 2/1989 | Kohn |
| 4,946,929 | A | 8/1990 | D'amore |
| 5,010,167 | A | 4/1991 | Eyal Ron |
| 5,019,379 | A | 5/1991 | Domb |
| 5,114,719 | A | 5/1992 | Sabel et al. |
| 5,208,111 | A | 5/1993 | Decher et al. |
| 5,364,634 | A | 11/1994 | Lew |
| 5,399,665 | A | 3/1995 | Barrera |
| 5,462,990 | A | 10/1995 | Hubbell et al. |
| 5,512,131 | A | 4/1996 | Kumar et al. |
| 5,512,600 | A | 4/1996 | Mikos |
| 5,514,378 | A | 5/1996 | Mikos |
| 5,518,767 | A | 5/1996 | Rubner et al. |
| 5,536,573 | A | 7/1996 | Rubner et al. |
| 5,630,941 | A | 5/1997 | Burger et al. |
| 5,660,873 | A | 8/1997 | Nikolaychik et al. |

(Continued)

FOREIGN PATENT DOCUMENTS

| | | |
|---|---|---|
| DE | 19812083 | 9/1999 |
| DE | 29907804 | 10/1999 |

(Continued)

OTHER PUBLICATIONS

Abeloff, M.D., et al., Chapter 95: Cancer of the Breast, in Abeloff's Clinical Oncology, Fourth Edition, pp. 1875-1943, Churchill Livingstone Elsevier (2008).

(Continued)

*Primary Examiner* — Gina Justice
(74) *Attorney, Agent, or Firm* — Foley Hoag LLP

(57) ABSTRACT

Provided are systems for controlled release of proteins from decomposable thin films constructed by layer-by-layer deposition. Such films generally comprise alternating layers of polymers and proteins, and may further comprise additional layers of polyions. In some embodiments, decomposable thin films and methods of using such films allow proteins to be released over an extended period of time and/or retention of as much as 100% of function of released protein.

31 Claims, 13 Drawing Sheets

(56) References Cited

U.S. PATENT DOCUMENTS

| | | |
|---|---|---|
| 5,696,175 A | 12/1997 | Mikos |
| 5,700,559 A | 12/1997 | Sheu et al. |
| 5,714,166 A | 2/1998 | Tomalia et al. |
| 5,716,404 A | 2/1998 | Vacanti |
| 5,716,709 A | 2/1998 | Ferguson et al. |
| 5,736,372 A | 4/1998 | Vacanti |
| 5,770,417 A | 6/1998 | Vacanti |
| 5,797,898 A | 8/1998 | Santini, Jr. et al. |
| 5,804,178 A | 9/1998 | Vacanti |
| 5,807,636 A | 9/1998 | Sheu et al. |
| 5,837,377 A | 11/1998 | Sheu et al. |
| 5,837,752 A | 11/1998 | Shastri |
| 5,858,746 A | 1/1999 | Hubbell et al. |
| 5,902,599 A | 5/1999 | Anseth |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri |
| 6,103,266 A | 8/2000 | Tapolsky et al. |
| 6,114,099 A | 9/2000 | Liu et al. |
| 6,123,681 A | 9/2000 | Brown, III |
| 6,123,727 A | 9/2000 | Vacanti |
| 6,131,211 A | 10/2000 | Hennessey |
| 6,180,239 B1 | 1/2001 | Whitesides et al. |
| 6,235,224 B1 | 5/2001 | Mathiowitz et al. |
| 6,312,727 B1 | 11/2001 | Schacht et al. |
| 6,402,918 B1 | 6/2002 | Schlenoff et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 | 5/2004 | Wolff et al. |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,896,926 B2 | 5/2005 | Qiu et al. |
| 6,919,373 B1 | 7/2005 | Lam et al. |
| 6,998,115 B2 | 2/2006 | Langer |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,303,814 B2 | 12/2007 | Lamberti et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,354 B2 | 9/2008 | Eto |
| 7,427,394 B2 | 9/2008 | Anderson |
| 7,491,263 B2 | 2/2009 | Wang et al. |
| 7,879,575 B2 | 2/2011 | Kricka et al. |
| 8,105,652 B2 | 1/2012 | Wood et al. |
| 2002/0053514 A1 | 5/2002 | Locascio et al. |
| 2002/0131933 A1 | 9/2002 | Delmotte |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0113368 A1 | 6/2003 | Nomoto et al. |
| 2003/0124368 A1 | 7/2003 | Lynn et al. |
| 2004/0013721 A1 | 1/2004 | Antipov |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2005/0019404 A1 | 1/2005 | Sung et al. |
| 2005/0152955 A1 | 7/2005 | Akhave et al. |
| 2005/0208100 A1 | 9/2005 | Weber et al. |
| 2005/0276841 A1 | 12/2005 | Davis et al. |
| 2006/0127437 A1 | 6/2006 | Kennedy et al. |
| 2006/0198897 A1 | 9/2006 | Pacetti |
| 2006/0216494 A1 | 9/2006 | Furedi-Milhofer et al. |
| 2006/0246112 A1 | 11/2006 | Snyder et al. |
| 2007/0020469 A1 | 1/2007 | Wood et al. |
| 2007/0077276 A1 | 4/2007 | Haynie |
| 2007/0083186 A1 | 4/2007 | Carter et al. |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2007/0276330 A1 | 11/2007 | Beck et al. |
| 2008/0139450 A1 | 6/2008 | Madhyastha et al. |
| 2008/0228280 A1 | 9/2008 | Cohen et al. |
| 2008/0248108 A1 | 10/2008 | Krotz et al. |
| 2008/0311177 A1 | 12/2008 | Hammond et al. |
| 2009/0053139 A1 | 2/2009 | Shi et al. |
| 2009/0061006 A1 | 3/2009 | Leuschner et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao |
| 2009/0246142 A1 | 10/2009 | Bhatia et al. |
| 2009/0258045 A1 | 10/2009 | Chuang et al. |
| 2009/0263468 A1 | 10/2009 | Mcanjulty et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0040674 A1 | 2/2010 | Smith et al. |
| 2010/0189683 A1 | 7/2010 | Holmlund et al. |
| 2011/0038939 A1 | 2/2011 | Lvov et al. |
| 2011/0114244 A1 | 5/2011 | Yoo et al. |
| 2011/0143127 A1 | 6/2011 | Gupta et al. |
| 2011/0301209 A1 | 12/2011 | Zaknoen et al. |
| 2012/0027837 A1 | 2/2012 | DeMuth et al. |
| 2012/0058355 A1 | 3/2012 | Lee et al. |
| 2012/0277719 A1 | 11/2012 | Shukla et al. |
| 2012/0277852 A1 | 11/2012 | Shukla et al. |
| 2013/0190890 A1 | 7/2013 | Shah et al. |
| 2013/0273137 A1 | 10/2013 | Mandell et al. |
| 2014/0011759 A1 | 1/2014 | Yaffe et al. |
| 2014/0039575 A1 | 4/2014 | Bradley et al. |
| 2014/0302116 A1 | 10/2014 | Castleberry et al. |
| 2014/0328931 A1 | 11/2014 | Hammond et al. |
| 2015/0125879 A1 | 5/2015 | Li et al. |

FOREIGN PATENT DOCUMENTS

| | | |
|---|---|---|
| EP | 0 443 809 | 8/1991 |
| EP | 1 116 516 | 7/2001 |
| EP | 2 162 283 | 9/2010 |
| EP | 2 566 468 | 3/2013 |
| EP | 2 701 908 | 3/2014 |
| GB | 1213803 | 11/1970 |
| GB | 1213805 | 11/1970 |
| WO | WO 95/11748 | 5/1995 |
| WO | WO 95/34595 | 12/1995 |
| WO | WO 96/03147 | 2/1996 |
| WO | WO 98/03573 | 1/1998 |
| WO | WO 98/17330 A1 | 4/1998 |
| WO | WO 98/47948 | 10/1998 |
| WO | WO 99/47253 | 9/1999 |
| WO | WO 99/56878 A1 | 9/1999 |
| WO | WO 99/59647 A1 | 11/1999 |
| WO | WO 00/77281 | 12/2000 |
| WO | WO 01/57118 | 8/2001 |
| WO | WO 01/94441 | 12/2001 |
| WO | WO 02/12888 A2 | 2/2002 |
| WO | WO 02/085500 | 10/2002 |
| WO | WO 03/035716 | 5/2003 |
| WO | WO 2006/051227 | 5/2006 |
| WO | WO 2006/086391 | 8/2006 |
| WO | WO 2007/140391 | 12/2007 |
| WO | WO 2007/140402 | 12/2007 |
| WO | WO 2008/057127 A2 | 5/2008 |
| WO | WO 2008/157372 | 12/2008 |
| WO | WO 2010/021973 | 2/2010 |
| WO | WO 2010/120531 | 10/2010 |
| WO | WO 2011/140136 | 11/2011 |
| WO | WO 2012/149492 | 11/2012 |

(56) References Cited

FOREIGN PATENT DOCUMENTS

| WO | WO 2012/149494 | 11/2012 |
|---|---|---|
| WO | WO 2013/110047 | 7/2013 |
| WO | WO 2013/163234 | 10/2013 |
| WO | WO 2014/059269 | 4/2014 |
| WO | WO 2014/066862 | 5/2014 |
| WO | WO 2014/150074 | 9/2014 |

OTHER PUBLICATIONS

Abramoff, M.D., et al., "Image Processing with ImageJ" Biophotonics International, 11:36-42 (2004).
Absolom, D.R., et al., "Protein Adsorption to Polymer Particles: Role of Surface Properties" J Biomed Mater Res., 2:161-71 (1987).
Afonin, K. A. et al., "In vitro Assembly of Cubic RNA-Based Scaffolds Designed in silico", Nature Nanotechnol, 5:676-682 (2010).
Ai, H., et al., Biomedical Applications of Electrostatic Layer-By-Layer Nano-Assembly of Polymers, Enzymes, and Nanoparticles Cell Biochem Biophys, 39(1):23-43 (2003).
Akinc, A. et al., "Synthesis of Poly(β-amino ester)s Optimized for Highly Effective Gene Delivery" Bioconjugate Chem., 14:979-988 (2003).
Akinc, A., et al., "A Combinatorial Library of Lipid-Like Materials for Delivery of RNAi Therapeutics", Nature Biotechnol., 26(5):561-569 (2008).
Albeck, J.G., et al., "Modeling a Snap-Action,Variable-Delay Switch Controlling Extrinsic Cell Death", PLoS Biology, 6(12):2831-2852 (2008).
Albrektsson, T., et al., "Osteoinduction, Osteoconduction and Osseointegration", Eur Spine J., 10:S96-S101 (2001).
Alsberg, E., et al., "Craniofacial Tissue Engineering", Critical Reviews in Oral Biology and Medicine : An Official Publication of the American Association of Oral Biologists 12(1): 64-75 (2001).
Alsberg, E., et al., "Regulating Bone Formation Via Controlled Scaffold Degradation", J Dent Res, 82(11): 903-908 (2003).
Alvarez-Román, R., et al., "Skin Penetration and Distribution of Polymeric Nanoparticles", J. Controlled Release, 99:53-62 (2004).
Alves, N.A., et al., "Self Assembling and Crosslinking of Polyelectrolyte Multilayer Films of Chitosan and Alginate Studied by QCM and IR Spectroscopy", Macromol Biosci, 9(8):776-85 (2009).
Anderson, D.G., et al., "Semi-Automated Synthesis and Screening of a Large Library of Degradable Cationic Polymers for Gene Delivery," Angew. Chem. Int. Ed., 42:3151-3158 (2003).
Anderson, W.F., "Human Gene Therapy" Nature, 392: 25-30 (1996).
Anderson, J.M. and Shive, M.S., "Biodegradation and Biocompatibility of PLA and PLGA Microspheres" Adv. Drug Delivery Rev. 28: 5-24, 1997.
Ando, S., et al., "PLGA Micospheres Containing Plasmid DNA: Preservation of Supercoiled DNA via Cryopreparation and Carbohydrate Stabilization" J. Pharm. Sci.,88: 126-130, (1999).
Antipov, A.A., et al., "Sustained Release Properties of Polyelectrolyte Multilayer Capsules" J. Phys. Chem., 105:2281-2284 (2001).
Ariga, K., et al., "Layer-By-Layer Assembly as a Versatile Bottom-Up Nanofabrication Technique for Exploratory Research and Realistic Application", Phys Chem Chem Phys., 9(19):2319-40 (2007).
Balabushevich, N.G., et al., "Protein-Loaded Microspheres Prepared by Sequential Adsorption of Dextran Sulphate and Protamine on Melamine Formaldehyde Core" J Microencapsul, 26(7):571-9 (2009).
Balko, J.M., et al., "Gene Expression Patterns that Predict Sensitivity to Epidermal Growth Factor Receptor Tyrosine Kinase Inhibitors in Lung Cancer Cell Lines and Human Lung Tumors", BMC Genomics, 7:289-302 (2006).
Barrera, D.A., et al., "Synthesis and RGD Peptide Modification of a New Biodegradable Copolymer: Poly(lactic acid-co-lysine)" J. Am. Chem. Soc., 115:11010-11011 (1993).

Baselga, J., et al., "Phase II Multicenter Study of the Antiepidermal Growth Factor Receptor Monoclonal Antibody Cetuximab in Combination With Platinum-Based Chemotherapy in Patients With Platinum-Refractory Metastatic and/or Recurrent Squamous Cell Carcinoma of the Head and Neck", Journal of Clinical Oncology, 23(4):5568-5577 (2005).
Bass, B.L., "RNA Interference the Short Answer", Nature 411:428-429 (2001).
Behr, J.-P., "Synthetic Gene-Transfer Vectors" Ace. Chem. Res., 26: 274-278 (1993).
Behr, J.-P., "The Proton Sponge: a Trick to Enter Cells the Viruses Did Not Expoit" Chimia, 51: 34-36 (1997).
Benkirane-Jessel, N., et al., "Build-up if Polypeptide Multilayer Coatings with Anti-Inflammatory Properties Based on the Embedding of Piroxicam-Cyclodextrin Complexes," Advanced Functional Materials., 14(2):174-182 (2004).
Berg, M.C., et al., "Controlling Mammalian Cell Interactions on Patterned Polyelectrolyte Multilayer Surfaces", Langmuir, 20(4):1362-8 (2004).
Bershteyn, A., et al., "Polymer-supported lipid shells, onions, and flowers", Soft Matter, 4:1787-1791 (2008).
Beyer, S., et al., "Periodic DNA Nanotemplates Synthesized by Rolling Circle Amplification", Nano Lett, 5(4):719-722 (2005).
Biggs, M.J.P., et al., "The Use of Nanoscale Topography to Modulate the Dynamics of Adhesion Formation in Primary Osteoblasts and ERK/MAPK Signalling in STRO-1+ Enriched Skeletal Stem Cells", Biomaterials, 30(28):5094-103 (2009).
Bins, A.D., et al., "A Rapid and Potent DNA Vaccination Strategy Defined by in vivo Monitoring of Antigen Expression", Nat. Med., 11:899-904 (2005).
Blacklock, J., et al., "Cross-Linked Bioreducible Layer-By-Layer Films for Increased Cell Adhesion and Transgene Expression", J Phys Chem B, 114(16):5283-91 (2010).
Boes, M., et al., "T-Cell Engagement of Dendritic Cells Rapidly Rearranges MHC Class II Transport", Nature, 418:983-988 (2002).
Bonewald, L.F., et al., "Von Kossa Staining Alone is Not Sufficient to Confirm that Mineralization In Vitro Represents Bone Formation" Calcif Tissue Int., 72(5):537-47 (2003).
Bott, A.W., "Applications of "Wired" Enzyme Electrodes," Current Separations, 21(1):3-6 (2004).
Boudou, T., et al., "Internal Composition Versus the Mechanical Properties of Polyelectrolyte Multilayer Films: The Influence of Chemical Cross-Linking" Langmuir, 25(24):13809-19 (2009).
Boudou, T., et al., "Multiple Functionalities of Polyelectrolyte Multilayer Films: New Biomedical Applications" Adv. Mater., 22(4):441-467 (2010).
Boussif, et al., "A Versatile Vector for Gene and Oligonucleotide Transfer into Cells in Culture and In Vivo: Polyethylenimine" Proc. Nat/. Acad. Sci, USA, 92: 7297-7301, 1995.
Brama, M., et al., "Effect of Titanium Carbide Coating on the Osseointegration Response in vitro and in vivo", Biomaterials, 28(4):595-608 (2007).
Brange, J. and Langkjaer, L., "Insulin Formulation and Delivery", Pharm Biotechnology, 10:343-409 (1997).
Brazeau, G.A., et al., "In Vitro Myotoxicity of Selected Cationic Macromolecules Used in Non-1tb1 Gene Delivery",Pharm. Res., 15: 680-684 (1998).
Brewer, L., et al., "Condensation of DNA by Spermatid Basic Nuclear Proteins", J Biol Chem., 277(41):38895-900 (2002).
Brewster, M.E. and Loftsson, T., "Cyclodextrins as Pharmaceutical Solubilizers," Advanced Drug Delivery.,59: 645-666 (2007).
Buser, H.J., et al., "The Crystal Structure of Prussian Blue: Fe4[Fe(CN)6]3xH20," Inorganic Chemistry, 16(11 ):2704-2710 (1977).
Calvo, E.J. and Wolosiuk, A., "Donnan Permselectivity in Layer-by-Layer Self-Assembled Redox Polyelectrolyte thin film", J. Am. Soc., 124: 8490-8497(2002).
Carey, L.A., et al., "EGFR Inhibition with Cetuximab Added to Carboplatin in Metastatic Triple-Negative (Basal-Like) Breast Cancer," Supplement to Journal of Clinical Oncology, ASCO Annual Meeting Proceedings, TBCRC 001: Clinical Science Symposium, 43S (2009).

(56) References Cited

OTHER PUBLICATIONS

Carpenter, M.K. and Conell, R.S., "A Single-Film Electrochromic Device," J. Electrochem. Soc., 137(8):2464-2467 (1990).
Carpenter, A. E. et al., CellProfiler: image analysis software for identifying and quantifying cell phenotypes, Genome Biology, 7(10):R100-R100.11 (2006).
Carragee E.J., et al. "A Critical Review of Recombinant Human Bone Morphogenetic Protein-2 Trials in Spinal Surgery: Emerging Safety Concerns and Lessons Learned", Spine J, 11(6): 471-491 (2011).
Carrell, D.T., et al., "The Aetiology of Sperm Protamine Abnormalities and Their Potential Impact on the Sperm Epigenome", Int J Androl., 31(6):537-45 (2008).
Caruso, F., "COLL 34-Polymer Design and Assembly for Next-Generation Particle Delivery", Abastracts of Papers American Chemical Society, 237th National Meeting of American Chemical Society, Salt Lake City Utah, Mar. 22, 2009.
Castleberry, S., et al., "Nanolayered siRNA Dressing for Sustained Localized Knockdown," *ACS Nano*, 7(6): 5251-5261 (2013).
Castleberry, S., et al., "Surface Mediated Delivery of siRNA from Layer-By-Layer Assembled Polyelectrolyte Films for the Acceleration of Wound Healing," Abstracts of Papers, 244th National Mtg & Exposition, (Aug. 19-23, 2012).
Cavalieri, F., et al., "Assembly and Functionalization of DNA-Polymer Microcapsules", ACS Nano, 3:234-240 (2009).
Chen, S.-M., "Preparation, Characterization, and Electrocatalytic Oxidation Properties of Iron, Cobalt, Nickel, and Indium Hexacyanoferrate," Journal of Electroanalytical Chemistry, 521:29-52 (2002).
Choksakulnimitr, S., et al., "In Vitro Cytotoxicity of Macromolecules in Different Cell Culture Systems", *Controlled Release*, 34: 233-241 (1995).
Chou, T.-C., et al., Quantitative Analysis of Dose-Effect Relationships: The Combined Effects of Multiple Drugs or Enzyme Inhibitors, Advances in Enzyme Regulation, 22:27-55 (1984).
Christensen, K., et al., "Heparin Coating of the Stent Graft—Effects on Platelets, Coagulation and Complement Activation," Biomaterials, 22:349-355 (2001).
Cini, N., et al., "Step-By-Step Assembly of Self-Patterning Polyelectrolyte Films Violating (Almost) All Rules of Layer-By-Layer Deposition", J Am Chem Soc., 132(24):8264-5 (2010).
Clark, S.L., et al., "Selective Deposition in Multilayer Assembly: SAMs as molecular templates," *Supramolecular Science*, 4(1-2):141-146 (1997).
Corkery, B.,et al., "Epidermal Growth Factor Receptor as a Potential Therapeutic Target in Triple-Negative Breast Cancer", *Annals of Oncology*, 20:862-867 (2009).
Cotten, M., et al., "Receptor-Mediated Transport of DNA into Eukaryotic Cells", *Methods Enzym*., 217:618-644 (1993).
Crane, N.J., et al., "Cyclodextrin Inclusion Complexes with a Solvatochromic Flurorescent Probe," *Journal of Chemical Education*,79(10):1261-1263 (2002).
Crouzier, T. and Picart, C., "Ion Pairing and Hydration in Polyelectrolyte Multilayer Films Containing Polysaccharides", Biomacromolecules, 10(2):433-42 (2009).
Crouzier, T., ct al., "The performance of BMP-2 Loaded TCP/HAP Porous Ceramics with a Polyelectrolyte Multilayer Dilm Coating", Biomaterials, 32(30): 7543-7554 (2011).
Crystal, R.G., "Transfer of Genes to Humans: Early Lessons and Obstacles to Success" *Science*, 270: 404-410 (1995).
Dalby, M.J., et al., "The Control of Human Mesenchymal Cell Differentiation Using Nanoscale Symmetry and Disorder", Nat Mater, 6(12):997-1003 (2007).
Danhier, F., et al., "PLGA-Based Nanoparticles: An Overview of Biomedical Applications", J Control Release, 161(2): 505-522 (2012).
Danusso, F. and Ferruti, P., "Synthesis of Tertiary Amine Polymers" *Polymer*, 11:88-113 (1970).
Daubendiek, S. L., et al., "Rolling-Circle RNA-Synthesis—Circular Oligonucleotides as Efficient Substrates for T7 RNA-Polymerase", J. Am. Chem. Soc., 117:7818-7819 (1995).

Davis, M.E. and Brewster, M.E., "Cyclodextrin-Based Pharmaceutics: Past, Present and Future," *Nature Reviews* (3), 1023-1035 (2004).
Davis, D., et al., "Challenges and potential for RNA nanoparticles (RNPs)", J Biomed Nanotechnol, 5(1):36-44 (2009).
Davis, M. E., et al., "Evidence of RNAi in Humans From Systemically Administered siRNA Via Targeted Nanoparticles", Nature, 464:1067-1070 (2010).
de Jonge, L.T., et al., "The Osteogenic Effect of Electrosprayed Nanoscale Collagen/Calcium Phosphate Coatings on Titanium", Biomaterials, 31(9):2461-9 (2010).
Decher, G. and Hong, J.-D., "Buildup of Ultrathin Multilayer Films by a Self-Assembly Process, 1 Consecutive Adsorption of Anionic and Cationic Bipolar Amphiphiles on Charged Surfaces," *Makromol. Chem., Macro mol. Symp*., 46:321-327 (1991).
Decher, G., et al., "Layer-By-Layer Assembled Multicomposite Films," Curr. Opinion Coli. & Interf. Sci., 3:32-39 (1998).
Decher, G., et al., "New Nanocomposite Films for Biosensors: Layer-By-Layer Adsorbed Films of Polyelectrolytes, Proteins or DNA," Biosensors & Bioelectronics, 9:677-684 (1994).
Decher, G., "Fuzzy Nanoassemblies: Toward Layered Polymeric Multicomposites" *Science*, 277: 1232-1237 (1997).
Decher, G. and Hong, J.-D., "Buildup of Ultrathin Multilayer Films by a Self-Assembly Process: II. Consecutive Adsorption of Anionic and Cationic Bipolar Amphiphiles and Polyelectrolytes on Charged Surfaces," Ber. Bunsenges. Phys. Chem., 95(11 ):1430-1434 (1991).
DeLongchamp, D.M., et al., "High-Contrast Electrochromism from Layer-By-Layer Polymer Films," Chem. Mater, 15:1575-1586 (2003).
DeLongchamp, D.M. and Hammond, P.T., "Fast Ion Conduction in Layer-By-Layer Polymer Films," Chem. Mater., 15:1165-1173 (2003).
DeLongchamp, D.M. and Hammond, P.T., "High-Contrast Electrochromism and Controllable Dissolution of Assembled Prussian Blue/Polymer Nanocomposites," Adv. Funct. Mater., 14(3):224-231 (2004).
Demeneix, B.A. and Behr, J.P., "The Proton Sponge: A Trick the Viruses Did Not Exploit," American Chemical Society, 146-151 (1996).
DeMuth, P.C., et al., "Nano-Layered Microneedles for Transcutaneous Delivery of Polymer Nanoparticles and Plasmid DNA", Adv Mater, 22(43):4851-6 (2010).
DeMuth, P.C., et al., "Polymer Multilayer Tattooing for Enhanced DNA Vaccination", Nature Materials, 12(4): 367-376 (2013).
Dent, R. et al., "Triple-Negative Breast Cancer: Clinical Features and Patterns of Recurrence," Clinical Cancer Research, 13: 4429-4434 (2007).
Deshmukh, H.M. and Huang, L., "Liposome and Polylysine Mediated Gene Transfer", *New J. Chem*.,21:113-124 (1997).
Diaz, R., et al., "Antitumor and Antiangiogenic Effect of the Dual EGFR and HER-2 Tyrosine Kinase Inhibitor Lapatinib in a Lung Cancer Model," *BMC Cancer*, 10:188 (2010).
Diegelman, A.M. and Kool, E.T., "Generation of Circular RNAs and Trans-Cleaving Catalytic RNAs by Rolling Transcription of Circular DNA Oligonucleotides Encoding Hairpin Ribozymes", Nucleic Acids Res., 26:3235-3241 (1998).
Dimitriou R., et al., "Bone Regeneration: Current Concepts and Future Directions", BMC Medicine, 9:66, 10 pages (2011).
Dimitrova, M., et al., "Sustained Delivery of siRNAs Targeting Viral Infection by Cell-Degradable Multilayered Polyelectrolyte Films", Proc. Natl. Acad. Sci. U.S.A., 105:16320-16325 (2008).
Dixon, M.C., "Quartz Crystal Microbalance with Dissipation Monitoring: Enabling Real-Time Characterization of Biological Materials and Their Interactions", J Biomol Tech., 19(3):151-8 (2008).
Doh, J. and Irvine, D. J., "Aqueous-Processible Photoresist Polymer for Multiple Protein Patterning: Synthesis, Characterization and Application to T Cell Activation", PMSE Prep, 93:327-328 (2005).
Doh, J. and Irvine, D. J., "Photogenerated Polyelectrolyte Bilayers From an AqueousProcessible Photoresist for Multicomponent Protein Patterning", J. Am. Chem. Soc., 126:9110-9171 (2004).
Dowben, R.M., "General Physiology: A Molecular Approach," *Division of Biological and Medical Sciences*, pp. 142-143, Harper & Row Publishers (1969).

(56) References Cited

OTHER PUBLICATIONS

Dubas, S.T., et al., "Multiple Membranes from 'True' Polyelectrolyte Multilayers", J. Am. Chem. Soc., 123:5368-5369 (2001).

Dubas, S.T. and Schlenoff, J.B., Polyelectrolyte Multilayers Containing a Weak Polyacid: Construction and Deconstruction, *Macromolecules*, 34: 3736-3740 (2001).

Duek, E.A.R., et al., "A Solid-State Electrochromic Device Based on Polyaniline, Prussian Blue and an Elastomeric Electrolyte," Advanced Materials, 5(9):650-652 (1993).

Ekins, S. et al., Pathway Mapping Tools for Analysis of High Content Data, Methods in Molecular Biology, 356:319-350 (2007).

Ekwueme, D.U., et al., "Model-Based Estimates of Risks of Disease Transmission and Economic Costs of Seven Injection Devices in Sub-Saharan Africa" Bull World Health Organ, 80:859-870 (2002).

Elbakry, A., et al., "Layer-By-Layer Assembled Gold Nanoparticles for siRNA Delivery", Nano Lett. 9:2059-2064 (2009).

Elbashir, S.M. et al., "Duplexes of 21-Nucleoties RNAs Mediate RNA Interference in Cultured Mammalian Cells", Nature 411:494-498 (2011).

Elbert, D.L. and Hubbell, J.A., "Self-Assembly and Steric Stabilization at Heterogeneous, Biological Surfaces Using Absorbing Block Copolymers" Chemistry & Biology, 5(3): 177-183 (1998).

El-Ghannam, A.R., et al., "Model Surfaces Engineered With Nanoscale Roughness and RGD Tripeptides Promote Osteoblast Activity", J Biomed Mater Res A., 68(4):615-27 (2004).

Ellis, D., et al., "Eietrochromism in the Mixed-Valence Hexacyanides. 1. Voltammetric and Spectral Studies of the Oxidation and Reduction of Thin Films of Prussian Blue," *J. Phys. Chem.* ,85:1225-1231 (1981).

Facca, S., et al., "Active Multilayered Capsules for In Vivo Bone Formation", Proc Natl Acad Sci USA, 107(8): 3406-3411 (2010).

Feiler, A.A., et al., "Adsorption and Viscoelastic Properties of Fractionated Mucin (BSM) and Bovine Serum Albumin (BSA) Studied With Quartz Crystal Microbalance (QCM-D)", J Colloid Interface Sci., 315(2):475-81 (2007).

Ferruti, P., et al., "Synthesis, Characterisation and Antitumour Activity of Platinum (II) Complexes of Novel Functionalised Poly (Arnido Amine)s", Macromol. Chem. Phys., 200:1644-1654 (1999).

Ferruti, P., et al., "Amphoteric Linear Poly(amido-amine)s as Endosomolytic Polymers: Correlation between Physicochemical and Biological Properties", Macromolecules, 33(21):7793-7800 (2000).

Ferruti, P. and Barbucci, R., "Linear Amino Polymers: Synthesis, Protonation and Complex Formation", *Advances in Polymer Science*, 58: 55-92 (1984).

Ferruti, P., et al., "Recent Results on Functional Polymers and Macromonomers offuterest as Biomaterials or for Biomaterial Modifcation" *Biomaterials*,15:1235-1241 (1994).

Ferruti, P., et al., "Synthesis, Physico-Chemical Properties and Biomedical Applications of Poly(amino-amine)s" Polymer, 26: 1336 (1985).

Fire, a., et al., "Potent and Specific Genetic Interference by Double-Stranded RNA in Caenorhabditis Elegans" *Nature*, 391: 806-811 (1998).

Fitzgerald, J.B., et al., "Systems Biology and Combination Therapy in the Quest for Clinical Efficacy", Nature Chemical Biology, 2(9):458-466 (2006).

Flessner, R.M., et al., "Degradable Polyelectrolyte Multilayers That Promote the Release of siRNA," Langmuir, 27(12): 7868-7876 (2011).

Freiberg, S. and Zhu, X.X., "Polymer Microspheres for Controlled Drug Release," Int. J. Pharm., 282:1-18 (2004).

Friedman, T., "Human Gene Therapy—An Immature Genie, But Certainly out of the Bottle", *Nature Med*, 2:144-147 (1996).

Gao, Q. and Yang, X., "Layer-By-Layer Electrodeposition of Redox Polymers and Enzymes on Screenprinted Carbon Electrodes for the Preparation of Reagentless Biosensors," ChemComm, 2 pages (2003).

Gaudet, S., et al., "A Compendium of Signals and Responses Triggered by Pro-death and Prosurvival Cytokines", Molecular & Cellular Proteomics, 4:1569-1590 (2005).

Gemici, Z., et al., "Hydrothermal Treatment of Nanoparticle Thin Films for Enhanced Mechanical Durability", Langmuir, 24(5):2168-77 (2008).

Gerasimov, O.V., et al., "Cytosolic Drug Delivery Using pH- and Light-Sensitive Liposomes", *Adv. Drug Delivery Rev.*, 38: 317-338 (1999).

Giljohann, D.A., et al., "Gene Regulation With Polyvalent siRNA-Nanoparticle Conjugates", J. Am. Chem. Soc., 131:2072-2073 (2009).

Gill, H.S. and Prausnitz, M.R., "Coated Microneedles for Transdermal Delivery", J. Controlled Release 117:227-237 (2007).

Gill, H.S., et al., "Cutaneous Vaccination Using Microneedles Coated With Hepatitis C DNA Vaccine", Gene Ther., 17:811-814 (2010).

Giudice, E.L. and Campbell, J.D., "Needle-Free Vaccine Delivery", Adv. Drug Delivery Rev., 2006, 58:68-89 (2006).

Glenn, G.M., et al., "Transcutaneous Immunization and Immunostimulant Strategies: Capitalizing on the Immunocompetence of the Skin", *Expert Rev. Vaccines*, 2:253-267 (2003).

Gonzalez, et al., "New Class ofPolymers for the Delivery ofMacromolecularTherapeutics" *Bioconjugate Chem.* 10: 1068-1074, 1999.

Grabow, W.W., et al., "siRNA Delivery: Loaded-Up Microsponges," Nature Materials, 11(4): 268-269 (2012).

Grabowski G. and Cornett, C.A., "Bone Graft and Bone Graft Substitutes in Spine Surgery: Current Concepts and Controversies", The Journal of the American Academy of Orthopaedic Surgeons, 21(1):51-60 (2003).

Graham, P.D., et al., "Phase Inversion Dynamics of PLGA Solutions Related to Drug Delivery," J Control Release, 58(2): 233-245 (1999).

Grayson, A.C.R., et al., "Electronic MEMS for Triggered Drug Delivery," Advanced Drug Delivery Reviews, 56:173-184 (2004).

Greenland, J.R., et al., "Beta-Amino Ester Polymers Facilitate In Vivo DNA Transfection and Adjuvant Plasmid DNA Immunization", *Mol. Ther*, 12:164-170 (2005).

Grewal, S.I. and Moazed, D., "Heterochromatin and Epigenetic Control of Gene Expression", Science, 301:798-802 (2003).

Guo, P., "RNA Nanotechnology: Engineering, Assembly and Applications in Detection, Gene Delivery and Therapy", J. Nanosci. Nanotechnol., 5:1964-1982 (2005).

Guo, P., "The Emerging Field of RNA Nanotechnology", Nature Nanotechnol., 5:833-842 (2010).

Guo, P., "Rolling Circle Transcription of Tandem siRNA to Generate Spherulitic RNA Nanoparticles for Cell Entry," Molecular Therapy, Nucleic Acids, 1:3162-2531 (2012).

Habib, M.A., et al., "A Tungsten-Trioxide/Prussian Blue Complementary Eletrochromic Cell with a Polymer Electrolyte," *Journal of Applied Electrochemistry*, 21:203-207 (1991).

Habib, M.A. and Maheswari, S.P., "Effect of Temperature on a Complementary W03-Prussian Blue Electrochromic System," *J. Electrochem. Soc.*, 139(8):2155-2157 (1992).

Haensler, J. and Szoka, Jr., F.C., "Polyamidoamine Cascade Polymers Mediate Efficient Transfection of Cells in Culture", Bioconjugate Chem., 4:372-379 (1993).

Hammond, P.T. and Whitesides, G.M., "Fromation of Polymer Microstructures by Selective Deposition of Polyion Multilayers Using Patterned Self-Assembled Monolayers as a Template," *Macromolecules*, 28:7569-7571 (1995).

Hammond, P.T., "Form and Function in Multilayer Assembly: New Applications at the Nanoscale," Adv. Mater., 16:1271-1293 (2004).

Hanahan, D. and Weinberg, R.A., "The Hallmarks of Cancer", Cell, 100:57-70 (2000).

Hanes, J., et al., "New Advances in Microsphere-Based Single-Dose Vaccines", *Adv. Drug Delivery Rev.*, 28:97-119 (1997).

Hansen, M.B., et al., "Re-Examination and Further Development of a Precise and Rapid Dye Method for Measuring Cell Growth/Cell Kill", *Immunol. Methods*,119:203-210 (1989).

Hag, M.I., et al., "Clinical Administration of Microneedles Skin Puncture, Pain and Sensation", *Biomed Microdevice*, 11:35-47 (2009).

Harper, J.W.and Elledge, S.J., "The DNA Damage Response: Ten Years After", Molecular Cell, 28(5):739-745 (2007).

(56) References Cited

OTHER PUBLICATIONS

Haynie, D.T., et al., "Protein-Inspired Multilayer Nanofilms: Science, Technology and Medicine", *Nanomedicine*,2(3):150-7 (2006).
Hehrlein, C., et al., "Drug-Eluting Stent: the "magic bullet" for Prevention of Restenosis?", Basic Res Cardiel, 97:417-423 (2002).
Helfrich, B.A., et al., "Antitumor Activity of the Epidermal Growth Factor Receptor (EGFR) Tyrosine Kinase Inhibitor Gefitinib (ZD1839, Iressa) in Non-Small Cell Lung Cancer Cell Lines Correlates with Gene Copy Number and EGFR Mutations But Not EGFR Protein Levels", Clinical Cancer Research, 12:7117-7125 (2006).
Heller, A., "Redox Hydrogel-Based Electrochemical Biosensore," Biosensors, Second Edition, pp. 1-18 (2004).
Hendrix, R.W., "Bacteriophage DNA Packaging: RNA Gears in a DNA Transport Machine", Cell, 94:147-150 (1998).
Hill, I.R.C., et al., "In Vitro Cytotoxicity ofPoly(amidoamine)s: Relevance to DNA Delivery" Biochim. Biophys., Acta, 1427:61-174 (1999).
Hillberg, A.L., et al., "Effect of Genipin Cross-Linking on the Cellular Adhesion Properties of Layer-By-Layer Assembled Polyelectrolyte Films", *Biomaterials*, 30(27):4463-70 (2009).
Hope, M.J., et al., "Cationic Lipids, Phosphatidylethanolamine and the Intracellular Delivery of Polymeric, Nucleic Acid-Based Drugs (Review)", *Molecular Membrane Technology*, 15:1-14 (1998).
Hossfeld, S., et al., "Bioactive Coronary Stent Coating Based on Layer-By-Layer Technology for SiRNA Release," *Acta Biomaterialia*, 9(5): 6741-6752 (2013).
Isakoff, S.J., "Triple Negative Breast Cancer: Role of Specific Chemotherapy", Cancer J., 16:53-61 (2010).
Itaya, K., et al., "Prussian-Blue-Modified Electrodes: An Application for a Stable Eletrochromic Display Device," J. Appl. Phys., 53:804-805 (1982).
Janes, K.A., et al., "A Systems Model of Signaling Identifies a Molecular Basis Set for Cytokine-lnduced Apoptosis", Science, 310:1646-1653 (2005).
Janes, K.A., et al., "Cytokine-lnduced Signaling Networks Prioritize Dynamic Range over Signal Strength", Cell, 135:343-354 (2008).
Jelle, B.P., et al., "Transmission Spectra of an Electrochromic Window Consisting of Polyaniline, Prussian Blue and Tungsten Oxide," Electrochimica Acta, 38(11 ):1497-1500 (1993).
Jessel, N., et al., "Multiple and Time-Scheduled In Situ DNA Delivery Mediated by B-cyclodextrin Embedded in a Polyelectrolyte Multilayer", PNAS, 103(23):8618-8621 (2006).
Jewell, C.M. and Lynn, D.M., "Multilayered Polyelectrolyte Assemblies as Platforms for the Selivery of DNA and Other Nucleic Acid-Based Therapeutics", *Adv. Drug Delivery Rev.*,60:979-999 (2008).
Jewell, C.M., et al., "Release of Plasmid DNA from Intravascular Stents Coated with Ultrathin Multilayered Polyelectrolyte Films", Biomacromolecules, 7:2483-2491 (2006).
Jewell, C.M., et al., "Multilayered Polyelectrolyte Films Promote the Direct and Localized Delivery of DNA to Cells", J. Controlled Release, 106:214-223 (2005).
Jiang, X. and Hammond, P.T.,, "Selective Deposition in Layer-by-Layer Assembly: Functional Graft," *Langmuir*, 16:8501-8509 (2000).
Johannsmann, D., et al., "Effect of Sample Heterogeneity on the Interpretation of QCM(-D) Data: Comparison of Combined Quartz Crystal Microbalance/Atomic Force Microscopy Measurements with Finite Element Method Modeling", *Anal Chem.*, 80(23):8891-9 (2008).
Johansen, P. et al. Antigen kinetics determines immune reactivity. Proc. Natl. Acad. Sci. U. S. A. 105,5189-5194,doi:10.1073/pnas.0706296105 (2008).
Kabanov, A.V. and Kabanov, V.A., "DNA Complexes with Polycations for the Delivery of Genetic Material inot Cells", Bioconjugate Chem., 6:7-20 (1995).
Kang, N., et al., "Inhibition of EGFR Signaling Augments Oridonin-Induced Apoptosis in Human Laryngeal Cancer Cells Via Enhancing Oxidative Stress Conicident with Activiation of Both the Intrinsic and Extrinsic Apoptotic Pathways", Cancer Letters, 294:147-158 (2010).

КаргИНа, О.В. СаморасЩЕπЛЯЮЩИЕСЯ ВО ДОРАСТВОРИМЫЕ ИОНОГЕННЫЕ πОЛИМЕРЫ Kaprnha (Kargina) "Self-Splitted Water-Soluble Lonogenic Polymers", Vysokomol. Soedin. Seriya A, 28:1139-1144 (1986). (with English abstract).
Kearney, C.J. and Mooney, D.J., "Macroscale Delivery Systems for Molecular and Cellular Payloads", Nat Mater, 12(11): 1004-1017 (2013).
Keselowsky, B.G., et al., "Integrin Alpha(5) Controls Osteoblastic Proliferation and Differentiation Responses to Titanium Substrates Presenting Different Roughness Characteristics in a Roughness Independent Manner", *J Biomed Mater Res A.*, 80(3):700-10 (2007).
Khan, Y., et al., "Tissue Engineering of Bone: Material and Matrix Considerations", J Bone Joint Surg Am, 90 Suppl 1:36-42 (2008).
Khopade, A.J. and Caruso, F., "Electrostatically Assembled Polyelectrolyte/Dendrimer Multilayer Films as Ultrathin Nanoreservoirs," *Nano Letters.*,2(4):415-418 (2002).
Kim, Y.-C., et al., "Enhanced Memory Responses to Seasonal H1N1 Influenza Vaccination of the Skin with the Use of Vaccine-Coated Microneedles", *J Infect Dis*, 201:190-198 (2010).
Kim, B.-S., et al., "Hydrogen-Bonding Layer-by-Layer-Assembled Biodegradable Polymeric Micelles as Drug Delivery Vehicles from Surfaces", *ACS Nano*,2(2):386-392 (2008).
Kim, B.-S., et al., "MAD (Multiagent Delivery) Nanolayer: Delivering Multiple Therapeutics from Hierarchically Assembled Surface Coatings", *Langmuir*, 25:14086-14092 (2009).
Kim, R., "Recent Advances in Understanding the Cell Death Pathways Activated by Anticancer Therapy", Cancer, 103(8):1551-1560 (2005).
Kinsella, Jr., C.R., et al., "BMP-2-Mediated Regeneration of Large-Scale Cranial Defects in the Canine: An Examination of Different Carriers", Plast Reconstr Surg, 127(5):1865-1873 (2011).
Klopman, G. and Zhu, H., "Recent Methodologies for the Estimation of N-Octanol/Water Partition Coefficents and their Use in the Prediction of Membrane Transport Properties of Drugs," Mini-Reviews in Medicinal Chemistry, 5:127-133 (2005).
Krebs, M.R.H., et al., "The Formation of Spherulites by Amyloid Fibrils of Bovine Insulin", Proc Natl Acad Sci USA, 101:14420-14424 (2004).
Krogman, K.C., et al., "Spraying Asymmetry into Functional Membranes Layer-By-Layer", *Nat. Mater.*, 8:512-518 (2009).
Krogman, K.C., et al., "Industrial-Scale Spray Layer-By-Layer Assembly for Production of Biomimetic Photonic Systems", Bioinspiration & Biomimetics, 8(4): 045005 11 pages (2013).
Kukowska-Latallo, J.F., et al., "Efficient Transfer of Genetic Material into Manunalian Cells Using Starburst Polyamidoamine Dendrimers", *Proc. Nat/. Acad. Sci. USA*, 93: 4897-4902 (1996).
Kumar, A. et al., "Patterning Self-Assembled Monolayers: Applications in Materials Science," Langmuir, 10:1498-1511 (1994).
Kwon, H.Y. and Langer, R., "Pseudopoly(amino acids): A Study of the Synthesis and Characterization of Poly(trans-4-hydroxy-N-acyi-L-proline esters)," Macromolecules, 22:3250-3255 (1989).
Landes, C.A., et al., "Maxillary and Mandibular Osteosyntheses with PLGA and P(L/DL)LA Implants: A 5-Year Inpatient Biocompatibility and Degradation Experience", Plastic and Reconstructive Surgery, 117(7): 2347-2360 (2006).
Langer, R., "Biomaterials in Drug Delivery and Tissue Engineering: One Laboratory's Experience," *Ace. Chem. Res.*, 33:94-101, (2000).
Langer, R., "Selected Advances in Drug Delivery and Tissue Engineering," *J. Control Release*,62:7-11 (1999).
LaVan, D.A., et al., "Small-Scale Systems for In Vivo Drug Delivery," Nature Biotechnology, 21(10):1184-1191 (2003).
Lavos-Valereto, I.C., et al., "In Vitro and In Vivo Biocompatibility Testing of Ti-6Al-7Nb Alloy With and Without Plasma-Sprayed Hydroxyapatite Coating", *J Biomed Mater Res.*, 58(6):727-33 (2001).
Lee, K., et al., "Growth Factor Delivery-Based Tissue Engineering: General Approaches and a Review of Recent Developments", Journal of the Royal Society Interface, 8(55): 153-170 (2011).
Lee, J.S., et al.," Gold, Poly(Beta-amino ester) Nanoparticles for Small Interfering RNA Delivery", Nano Lett., 9:2402-2406 (2009).

(56) References Cited

OTHER PUBLICATIONS

Lee, J.B., et al., "Self-assembled RNA interference microsponges for efficient siRNA delivery," Nature Materials, 11(4): 316-322 (2012).
Leguen, E., et al., "Bioactive Coatings Based on Polyelectrolyte Multilayer Architectures Functionalized by Embedded Proteins, Peptides or Drugs" *Biomol Eng.*, 24(1):33-41 (2007).
Liang, F.F., et al., "The Minimal Functional Sequence of Protamine", *Biochem. Biophys. Res. Commun.*, 336:653-659 (2005).
Liao, H., et al., "Response of Rat Osteoblast-Like Cells to Microstructured Model Surfaces In Vitro", *Biomaterials.*, 24(4):649-54 (2003).
Lichter, A.S. and Lawrence, T.S., "Recent Advances in Radiation Oncology", New England Journal of Medicine, 332(6):371-379 (1995).
Lim, Y.-B., et al., "A Self-Destroying Polycationic Polymer: Biodegradable Poly(4-Hydroxy-LProline Ester)", *J Am. Chem. Soc.*,121: 5633-5639 (1999).
Lim, Y.-B., et al., "Cationic Hyperbranched Poly(amino ester): A Novel Class of DNA Condensing Molecule with Catioic Surface, Biodegradable Three-Dimensional Structure, and Tertiary Amine Groups in the Interior" J. Am. Chem. Soc., 123:2460-61 (2001).
Lim, Y.-B.,et al., "Development of a Safe Gene Delivery System Using Biodegradable Polymer, Poly [a-(4-Aminobutyl-L-Glycolic Acid]", JAm. Chem. Soc., 122: 6524-6525 (2000).
Lin, C.-C. and Anseth, K.S., "PEG Hydrogels for the Controlled Release of Biomolecules in Regenerative Medicine," Pharmaceutical Research, 26(3): 631-643 (2009).
Linhardt, J.G., et al., "Free-Radical Synthesis ofPoly(2-Ethylacrylic Acid) Fractions of Low Polydispersity: Effects of Molecular Weight and Polydispersity on the pH-Dependent Conformational Transition in Aqueous Solution", *Macromolecules*,32: 4457-4459 (1999).
Linhardt, J.G. and Tirrell, D.A., "pH-Induced Fusion and Lysis ofPhosphatidylcholine Vesicles by Hydrophobic Polyelectrolyte Poly(2-ethylacrylic Acid)", *Langmuir*,16: 122-127 (2000).
Liu, X., et al., "Ultrathin Multilayered Films that Promote the Release of Two DNA Constructs with Separate and Distinct Release Profiles", Adv. Mater., 20:4148-4153 (2008).
Livingstone, D.J., et al., "Cationic Hyperbranched Poly(amino ester): A Novel Calss of DNA Condensing Molecule with Cationic Surface, Biodegradable Three-Dimensional Structure, and Tertiary Amine Groups in the Interior,"*J. Curr. Top. Med. Chem.*, 3:1171-1192 (2003).
Lo, H., et al., "Fabrication of controlled release biodegradable foams by phase separation," Tissue Eng., 1(1):15-28 (1995).
Lopez, J.P., et al., "Gefitinib Inhibition of Drug Resistance to Doxorubicin by Inactivating ABCG2 in Thyroid Cancer Cell Lines", Archives of Otolaryngology—Head & Neck Surgery, 133(10):1022-1027 (2007).
Luo, D. and Salzman, W.M., "Synthetic DNA Delivery Systems" *Nat. Biotechnol.*, 18: 33-37 (2000).
Lynn, D.M. and Langer, R., "Degradable Poly(β-amino esters): Synthesis, Characterization, and Self-Assembly with Plasmid DNA," *J. Am. Chem. Soc.*,122:10761-10768 (2000).
Lynn, D.M., et al., "pH-Responsive Polymer Microspheres: Rapid Release of Encapsulated Material Within the Range of Intracellular pH" Angewandte Chemie International Edition, 40:1707-1710 (2001).
Lynn, D.M., "Peeling Back the Layers: Controlled Erosion and Triggered Disassembly of Multilayered Polyelectrolyte Thin Films", Adv. Mater., 19:4118-4130 (2007).
Lynn, D.M., et al., "Accelerated Discovery of Synthetic Transfection Vectors: Parallel Synthesis and Screening of a Degradable Polymer Library", Journal of the American Chemical Society, 123:8155-8156 (2001).
Lynn, D.M., Construction of Degradable Thin Films via Layber-by-Layer Deposition of Polyelectrolytes: Fabrication, Characterization, and Application to Controlled Release, MIT Proposal 2001.
MacBeath, G., "Protein microarrays and proteomics", Nature Genetics Supplement, 32:526-532 (2002).

Macdonald, M., et al., "Release of a Model Protein From Biodegradable Self Assembled Films for Surface Delivery Applications", *J Control Release.*, 131(3):228-34 (2008).
MacDonald, M.L., et al.,"Tissue Integration of Growth Factor-Eluting Layer-by-Layer Polyelectrolyte Multilayer Coated Implants," *Biomaterials*, 32(5): 1446-1453 (2010).
Mansouri, S., et al., "Modulating the Release Kinetics Through the Control of the Permeability of the Layer-By-Layer Assembly: A Review", *Expert Opin Drug Deliv.*, 6(6):585-97 (2009).
Martin et al., "Solubility and Kinetic Release Studies of Naproxen and Ibuprofen in Soluble Epichlorohydrin-β-cyclodextrin Polymer," *Supramolecular Chemistry*. 18(8): 627-631, (2006).
Martinez, J., et al., "Single-Stranded Antisense siRNAs Guide Target RNA Cleavage in RNAi", Cell, 110:563-574 (2002).
Martino, M.M., et al., "Engineering the Growth Factor Microenvironment with Fibronectin Domains to Promote Wound and Bone Tissue Healing", Sci Transl Med, 3(100): 100ra189, 8 pages (2011).
Mathiowitz, E. and Langer, R., "Polyanhydride Microspheres as Drug Carriers I. Hot-Melt Microencapsulation", *J. Controlled Release*, 5:13-22 (1987).
Mathiowitz, E., et al., "Polyanhydride Microspheres as Drug Carriers. II. Microencapsulation", *J. Appl. Polymer Sci.*, 35: 755-774 (1988).
Mehrotra, S., et al., "Time Controlled Protein Release from Layer-by-Layer Assembled Multilayer Functionalized Agarose Hydrogels", *Adv Funct Mater.*, 20(2):247-58 (2010).
Mendelsohn, J.D., et al., "Rational Design of Cytophilic and Cytophobic Polyelectrolyte Multilayer Thin Films", *Biomacromolecules*, 4(1):96-106 (2003).
Michel, B., et al., "Printing Meets Lithography: Soft Approaches to High-Resolution Patterning", IBM Journal of Research and Development, 45(5): 697-719 (2001).
Mikos, A.G., et al., "Preparation and Characterization of Poly(L-Lactic Acid) Foams," Polymer 35(5): 1068-1077 (1994).
Mikszta, J.A., et al., "Improved Genetic Immunization Via Micromechanical Disruption of Skin-Barrier Function and Targeted Epidermal Delivery", *Nat. Med.*, 8:415-419 (2002).
Milano, G., et al., EGFR-Targeting Drugs in Combination With Cytotoxic Agents: From Bench to Bedside, A Contrasted Reality, British Journal of Cancer, 99:1-5 (2008).
Miller, "Cationic Liposomes for Gene Therapy" Angew. Chem. Int. Ed. 37: 1769-1785, 1998.
Mistry, A.S. and Mikos, A.G., "Tissue Engineering Strategies for Bone Regeneration", Advanced Biotech Engin/Biotechnol, 94:1-22 (2005).
Mizushima, N. et al., Methods in Mammalian Autophagy Research, Cell, 140:313-326 (2010).
Mok, H., et al., "Multimeric Small Interfering Ribonucleic Acid for Highly Efficient Sequence-Specific Gene Silencing", Nature Mater, 9:272-278 (2010).
Montesano, R., et al., "Test for Malignant Transformation of Rat Liver Cells in Culture: Cytology, Growth in Soft Agar, and Production of Plasminogen Activator," *Journal of the National Cancer Institute*, 59(6): 1651-1658 (1977).
Moor, A.N., et al., "Proteolytic Activity in Wound Fluids and Tissues Derived from Chronic Venous Leg Ulcers," *Wound Repair and Regeneration*, 17(6): 1067-1927 (2009).
Moran, M.C., et al., "Mixed Protein Carriers for Modulating DNA Release", Langmuir, 25(17):10263-70 (2009).
Morgillo, F., et al., "Antitumor Activity of Bortezomib in Human Cancer Cells With Acquired Resistance to Anti-Epidermal Growth Factor Receptor Tyrosine Kinase Inhibitors", Lung Cancer, 71 :283-290 (2011).
Moriguchi, I., et al., "Synthesis of Ultrathin Films of Prussian Blue by Successive Ion Adsorption Technique," Chemistry Letters, 31(3):310-311 (2002).
Morris, K.V., et al., "Small Interfering RNA-Induced Transcriptional Gene Silencing in Human Cells", Science, 305:1289-1202 (2004).
Moskowitz, J.S., et al., "The Effectiveness of the Controlled Release of Gentamicin From Polyelectrolyte Multilayers in the Treatment of *Staphylococcus aureus* Infection in a Rabbit Bone Model", *Biomaterials*, (23):6019-30 (2010).

(56) References Cited

OTHER PUBLICATIONS

Mulligan, R.C., "The Basic Science of Gene Therapy" *Science*,260: 926-932 (1993).
Murphy, J.E., et al., "A Combinatorial Approach to the Delivery of Efficient Cationic Peptoid Reagents for Gene Delivery", *Proc. Natl. Acad. Sci. USA*, 95: 1517-1522 (1998).
Nagashima, S., et al., "BCRP/ABCG2 Levels Account for the Resistance to Topoisomerase I Inhibitors and Reversal Effects by Getfitinib in Non-Small Cell Lung Cancer", Cancer Chemother Pharmacol, 58:594-600 (2006).
Neovius, E. and Engstrand, T., "Craniofacial Reconstruction With Bone and Biomaterials: Review Over the Last 11 Years", Journal of Plastic, Reconstructive & Aesthetic Surgery 63(10):1615-1623 (2010).
Neve, R.M. et al., "A Collection of Breast Cancer Cell Lines or the Study of Functionally Distinct Cancer Subtypes", Cancer Cell, 10:515-527 (2006).
Nevins, M., et al., "Platelet-Derived Growth Factor Stimulates Bone Fill and Rate of Attachment Level Gain: Results of a Large Multicenter Randomized Controlled Trial", J Periodontol, 76(12): 2205-2215 (2005).
Newman, D.J., et al., "Natural Products as Sources of New Drugs over the Period 1981-2002," *Journal of Natural Products*, 66:1022-1037 (2003).
Nguyen, P.M., et al., "Extended Release Antibacterial Layer-by-Layer Films Incorporating Linear-Dendritic Block Copolymer Micelles," *Chemistry of Materials*, 19:5524-5530 (2007).
Niemiec, W., et al., "Nanoheterogeneous Multilayer Films With Perfluorinated Domains Fabricated Using the Layer-By-Layer Method", Langmuir, 26(14):11915-20 (2010).
O'Donnell, P.B. and McGinity, J.W., "Preparation of Microspheres by the Solvent Evaporation Technique", *Adv. Drug Delivery Rev.*,28:25-42 (1997).
Oh, S., et al., "Stem Cell Fate Dictated Solely by Altered Nanotube Dimension", *Proc Natl Acad Sci USA*,106(7):2130-5 (2009).
Okada, H., "One-and Three-Month Release Injectable Microspheres of the LH-RH Superagonist Leuprorelin Acetate", *Adv. Drug Delivery Rev.*,28:43-70 (1997).
Oliva, G., et al., "Antiproliferative Drug-Eluting Stents: Systematic Review of the Benefits and Estimate of Economic Impact," Rev Esp Cardiel, 57(7):617-628 (2004).
Papanas, N. and Maltezos E., "Benefit-Risk Assessment of Becaplermin in the Treatment of Diabetic Foot Ulcers", Drug Safety, 33(6): 455-461 (2010).
Pareta, R.A., et al., "An Understanding of Enhanced Osteoblast Adhesion on Various Nanostructured Polymeric and Metallic Materials Prepared by Ionic Plasma Deposition", *J Biomed Mater Res A*,92(3):1190-201 (2010).
Park, J.-H., et al., "Biodegradable Polymer Microneedles: Fabrication, Mechanics and Transdermal Drug Delivery", *J. Controlled Release*, 104:51-66 (2005).
Park, J.-W., et al., "Osteoconductivity of Hydrophilic Microstructured Titanium Implants with Phosphate Ion Chemistry", *Acta Biomater*,5(6):2311-21 (2009).
Park, J.-H., et al., "Polymer Microneedles for Controlled-Release Drug Delivery", Pharm. Res., 23:1008-1019 (2006).
Pasco, N., et al., "Characterization of a Thermophilic L-Glutamate Dehydrogenase Biosenor for Amperometric Determination of L-Glutamate by Flow Injection Analysis," Biosensors & Bioelectronics, 14:171-178 (1999).
Pashuck, E.T. and Stevens, M.M., "Designing Regenerative Biomaterial Therapies for the Clinic", Science Translational Medicine, 4(160): 160sr164, 12 pages (2012).
Patil, M.L., et al., "Surface-Modified and Internally Cationic Polyamidoamine Dendrimers for Efficient siRNA Delivery", Bioconjug Chem, 19:1396-1403 (2008).
Pawson, T. and Linding, R., "Network Medicine", FEBS Letters, 582:1266-1270 (2008).

Pearton, M.,et al., "Gene Delivery to the Epidermal Cells of Human Skin Explants Using Microfabricated Microneedles and Hydrogel Formulations", *Pharm. Res*, 25(2):407-416 (2008).
Peer, D., et al., "Selective Gene Silencing in Activated Leukocytes by Targeting siRNAs to the Integrin Lymphocyte Function-Associated Antigen-1", Proc Natl Acad Sci USA, 104(10):4095-100 (2007).
Peer, D., et al., "Systemic Leukocyte-Directed siRNA Delivery Revealing Cyclin D1 as an Anti-Inflammatory Target", Science, 319:627-630 (2008).
Peerce, P.J and Bard, A.J., "Polymer Films on Electrodes, Part Ill. Digital Simulation Model for Cyclic Voltammetry of Electroactive Polymer Film and Electrochemistry of Poly(vinylferrocene) on Platinum," J. Electroanal. Chem, 114:89-115 (1980).
Perou, C.M., et al., "Molecular Portraits of Human Breast Tumours", Nature, 406:747-752 (2000).
Petrie, T.A., et al., "The Effect of Integrin-Specific Bioactive Coatings on Tissue Healing and Implant Osseointegration", *Biomaterials*, (19):2849-57 (2008).
Pfeifer, B.A., et al., "Formulation and Surface Modification of Poly-(ester-anhydride) Micro- and Nanoshperes," Biomaterials, 26:117-124 (2005).
Picart, C., et al., "Molecular Basis for the Explanation of the Expotential Growth of Polyelectrolyte Multilayers", PNAS 99(20):12531-12535 (2002).
Place, E.S., et al., "Complexity in Biomaterials for Tissue Engineering", Nat Mater, 8(6): 457-470 (2009).
Poerner, T.C., et al., "Drug-Coated Stents," Minimally Invasive Therapy & Allied Technologies, 11(4):185-192 (2002).
Porcel, C., et al., "From Exponential to Linear Growth in Polyelectrolyte Multilayers", Langmuir, 22(9):4376-83 (2006).
Porcel, C., et al., "Influence of the Polyelectrolyte Molecular Weight on Exponentially Growing Multilayer Films in the Linear Regime", *Langmuir*, 23(4):1898-904 (2007).
Porter, J.R., et al., "Bone Tissue Engineering: A Review in Bone Biomimetics and Drug Delivery Strategies", Biotechnology Progress, 25(6): 1539-1560 (2009).
Portin, L., "Layer-By-Layer Assembly of the Polyelectrolytes on Mesoporous Silicon Nanoparticles", Unpublixhed Master's Thesis, University of Eastern Finland, Joensuu, Finland (2012).
Prausnitz, M.R., "Microneedles for Transdermal Drug Delivery", *Adv. Drug Delivery Rev*, 56:581-587 (2004).
Prausnitz, M.R. and Langer, R., "Transdermal Drug Delivery", *Nat. Biotechnol*., 26:1261-1268 (2008).
Prüss-Üstün, A., et al., "WHO Environmental Burden of Disease Series", World Health Organization, Geneva 2003, 71 pages.
Putnam, D. and Langer, R., "Poly(4-hydroxy-L-proline ester): Low-Temperature Polycondensation and Plasmid DNA Complexation," Macromolecules, 32:3658-3662 (1999).
Qiu, E., et al., "Studies on the Drug Release Properties of Polysaccharide Multi layers Encapsulated Ibuprofen Microparticles", Langmuir, 17: 5375-5380 (2001).
Quan, F.-S., et al., "Stabilization of Influenza Vaccine Enhances Protection by Microneedle Delivery in the Mouse Skin", *PLoS One*, 4(9):e7152, 10 pages (2009).
Quarles, L.D., et al., "Distinct Proliferative and Differentiated Stages of Murine MC3T3-E1 Cells in Culture: An In Vitro Model of Osteoblast Development", *J Bone Miner Res*., (6):683-92 (1992).
Rajan, K.P. and Neff, V.D., "Electrochromism in the Mixed-Valence Hexacyanides. 2. Kinetics of the Reduction of Ruthenium Purple and Prussian Blue," J. Phys. Chem., 86:4361-4368 (1982).
Ramaswamy, Y., et al., "Sphene Ceramics for Orthopedic Coating Applications: An In Vitro and In Vivo Study", *Acta Biomater*, 5(8):3192-204 (2009).
Rao, W. and Smith, D.J., "Poly (Butaneodiol Spermate): A Hydrolytically Labile Polyester-Based Nitric Oxide Carrier", J. Bioactive and Compatible Polymers, 14: 54-63, 1999.
Rausch-fan, X., et al., "Differentiation and Cytokine Synthesis of Human Alveolar Osteoblasts Compared to Osteoblast-Like Cells (MG63) in Response to Titanium Surfaces", *Dent Mater*., 24(1):102-10 (2008).
Razzacki, S.Z., et al., "Integrated Microsystems for Controlled Drug Delivery," Advanced Drug Delivery Reviews, 56:185-198 (2004).

(56) References Cited

OTHER PUBLICATIONS

Richards, K. E., et al., "Mode of DNA Packing Within Bacteriophage Heads", J. Mol. Biol,. 78:255-259 (1973).
Richert, L., et al., "Cell Interactions with Polyelectrolyte Multilayer Films", *Biomacromolecules*, 3(6):1170-8 (2002).
Roach, P., et al., "Interpretation of Protein Adsorption: Surface-Induced Conformational Changes", *J Am Chem Soc.*, 127(22):8168-73 (2005).
Roach, P., et al., "Modern Biomaterials: A Review—Bulk Properties and Implications of Surface Modifications", *J Mater Sci Mater Med.*, 18(7):1263-77 (2007).
Roberts, J.C., et al., "Preliminary Biological Evaluation ofPolyamidoamine (P AMAM) Starburst TM Dendrimers" *J. Biomed. Mater. Res.*, 30: 53-65, (1996).
Robin, M.B., "The Color and Electronic Configurations of Prussian Blue," Electronic Configurations of Prussian Blue, 1(2):337-342 (1962).
Rohanizadeh, R., et al., "Gelatin Sponges (Gelfoam®) as a Scaffold for Osteoblasts", *J. Mater Sci. Mater Med.*, 19:1173-1182 (2008).
Rusnak, D.W. et al., Assessment of epidermal growth factor receptor (EGFR, ErbB1) and HER2 (ErbB2) protein expression levels and response to lapatinib (Tykerb®, GW572016) in an expanded panel of human normal and tumour cell lines, Cell Proliferation, 40: 580-594 (2007).
Sachs, K. et al., Casual Protein-Signaling Networks Derived from Multiparameter Single-Cell Data, Science, 308:523-529 (2005).
Saha, K., et al., "Designing Synthetic Materials to Control Stem Cell Phenotype", *Curr Opin Chem Biol.*, 11(4):381-7 (2007).
Sallusto, F., et al., "Central Memory and Effector Memory T Cell Subsets: Function, Generation, and Maintenance", Annu Rev. Immunol., 22:145-163 (2004).
Samuel, R.E. et al., "Osteoconductive Protamine-Based Polyelectrolyte Multilayer Functionalized Surfaces", Biomoteriols, 32:1491-1502 (2011).
Sanford, J.C., "The Biolistic Process", Trends Biotechnol., 6:288-302 (1988).
Santini, Jr., J.T., et al.,"Microchips as Controlled Drug-Delivery Devices," Angew. Chem. Int. Ed., 39:2396-2407 (2000).
Santini, Jr., J.T., et al., "Microchips for Drug Delivery," Abstracts of Papers of the American Chemical Society, 219(174):U34-U34 (2000).
Sapi, E., et al., "Ets-2 Transdominant Mutant Abolishes Anchorage-independent Growth and Macrophage Colony-stimulating Factor-stimulated Invasion by BT20 Breast Carcinoma Cells", Cancer Research, 58:1027-1033 (1998).
Sato, K., et al., "Layered Assemblies Composed of Sulfonated Cyclodextrin and Poly(allyamine)," Colloid & Polymer Science, 282:287-290 (2003).
Schaffer, et al., "Vector Unpacking as a Potential Banier for Receptor-Mediated Polyplex Gene Delivery"*Biotechnol. Bioeng.*, 61: 598-606 (000).
Schechter, A.L. et al., The *neu* oncogene: an erb-8-related gene encoding a 185,000-Mr tumour antiQen, Nature, 312:513-516 (1984).
Schlenoff, J.B., "Retrospective on the Future of Polyelectrolyte Multilayers", *Langmuir*, 25(24):14007-10 (2009).
Schmidt, D.J., et al., "Electrochemically Controlled Swelling and Mechanical Properties of a Polymer Nanocomposite", *ACS Nano.*, 3(8):2207-16 (2009).
Schmitz, J.P. and Hollinger, J.O., "The Critical Size Defect as an Experimental-Model for Craniomandibulofacial Nonunions", Clinical Orthopaedics and Related Research, 205: 299-308 (1986).
Schüler, C. and Caruso, F., "Decomposable Hollow Biopolymer-Based Capsules", Biomacromolecules, 2:921-26 (2001).
Schwarz, F., et al., "Potential of Chemically Modified Hydrophilic Surface Characteristics to Support Tissue Integration of Titanium Dental Implants", *J Biomed Mater Res B Appl Biomater.*, 88(2):544-57 (2009).

Schweikl, H. and Schmalz, G., "Triethylene Glycol Dimethacrylate Induces Large Deletions in the Hprt Gene of V79 Cells" *Mutat. Res.*,438: 71-78 (1999).
Seeman, N.C., "Nanomaterials Based on DNA", Annu. Rev. Biochem., 79:65-87 (2010).
Semple, S.C., et al., "Rational Design of Cationic Lipids for siRNA Delivery", Nature Biotechnol., 28:172-176 (2010).
Sengupta, S. et al., "Temporal Targeting of Tumor Cells and Neovasculature With a Nanoscale Delivery System", Nature, 436:568-572 (2005).
Seo, J., et al., "Effect of the Layer-By-Layer (LbL) Deposition Method on the Surface Morphology and Wetting Behavior of Hydrophobically Modified PEO and PAA LbL Films", *Langmuir*, 24(15):7995-8000 (2008).
Sevecka, M. and MacBeath, G., "State-Based Discovery: A Multidimensional Screen for Small-Molecule Modulators of EGF Signaling", Nature Methods, 3(10):825-831 (2006).
Seyhan, A.A., et al., "RNA Interference From Multimeric shRNSs Generated by Rolling Circle Transcripotion," *Oligonucleotides*,16(4): 353-363 (2006).
Shah, N.J., et al., "Surface-Mediated Bone Tissue Morphogenesis from Tunable Nanolayered Implant Coatings", Science Translational Medicine, 5(191):10 pages (2013).
Shi, Z., et al., "The Epidermal Growth Factor Tyrosine Kinase Inhibitor AG1478 and Erlotinib Reverse ABCG2-Mediated Drug Resistance", Oncology Reports, 21:483-489 (2009).
Shiratori, S.S. and Rubner, M.F., "pH-Dependent Thickness Behavior of Sequentially Adsorbed Layers of Weak Polyelectrolytes," Macormolecules, 33:4213-4219 (2000).
Shukla, A., et al., "Tunable Vancomycin Releasing Surfaces for Biomedical Applications", Small Nano Mirco, 21(6):2392-2404 (2010).
Shukla, A., et al., "Controlling the Release of Peptide Antimicrobial Agents from Surfaces", *Biomaterials*, 31(8):2348-2357 (2010).
Shutava, T.G., et al., "Layer-by-Layer-Coated Gelatin Nanoparticles as a Vehicle for Delivery of Natural Polyphenols", *ACS Nano.*, 3(7):1877-85 (2009).
Singh, M., et al., "Cationic Microparticles: A Potent Delivery System for DNA Vaccines", *Proc. Nat/. Acad. Sci. USA*, 97: 811-816 (2000).
Slamon, D.J., et al., "Human Breast Cancer: Correlation of Relapse and Survival with Amplification of the HER -2/neu Oncogene", Science, 235:177-182 (1987).
Smiell, J.M., et al., "Efficacy and Safety of Becaplermin (Recombinant Human Platelet-Derived Growth Factor-BB) in Patients With Nonhealing, Lower Extremity Diabetic Ulcers: A Combined Analysis of Four Randomized Studies", Wound Repair and Regeneration 7(5): 335-346 (1999).
Smith, R.C., et al., "Layer-by-Layer Platform Technology for Small-Molecule Delivery", Angew.Chem.Int.Ed., 48:8974-8977 (2009).
Smith, K.A., et al., "Enhancing ONA Vaccination by Sequential Injection of Lymph Nodes With Plasmid Vectors and Peptides", Vaccine, 27:2603-2615 (2009).
Smith, K.A., et al., "Multivalent Immunity Targeting Tumor-Associated Antigens by Intra-Lymph Node DNA-Prime, Peptide-Boost Vaccination", Cancer Gene Ther., 18: 63-76 (2011).
Song, J., et al., "Growth of Endothelial Cell on the Surface of Intravascular Sent Material: Bionic Construction of Bioactive Extracellular Matrix", Journal of Clinical Rehabilitative Tissue Engineering Research, 13(43):8425-8431 (2009).
Sordella, R., et al., "Gefitinib-Sensitizing EGFR Mutations in Lung Cancer Activate Anti-Apoptotic Pathways", Science, 305:1163-1167 (2004).
Spicer, P.P., et al., "Evaluation of Bone Regeneration Using the Rat Critical Size Calvarial Defect", Nature Protocols, 7(10): 1918-1929 (2012).
Stevens, M.M., "Biomaterials for Bone Tissue Engineering", Materials Today, 11(5): 18-25 (2008).
Strathmann, H., "Membrane Separation Processes: Current Relevance and Future Opportunities", AICHE Journal, 47(5): 1077-1087 (2001).
Stubbs, M.T., et al, "The Interaction of Thrombin With Fibrinogen", Eur. J. Biochem., 206: 187-195 (1992).

(56) References Cited

OTHER PUBLICATIONS

Su, X., et al., "Layer-By-Layer-Assembled Multilayer Films for Transcutaneous Drug and Vaccine Delivery", *ACS Nano*, 3:3719-3729 (2009).

Subramanian, A,. et al., "Gene Set Enrichment Analysis: A Knowledge-Based Approach for Interpreting Genome-Wide Expression Profiles", Proceedings of the National Academy of Sciences of the USA, 102(43):15545-15550 (2005).

Sullivan, S.P., et al., "Dissolving Polymer Microneedle Patches for Influenza Vaccination", Nat Med., 16:915-920 (2010).

Sullivan, S.P., et al., "Minimally Invasive Protein Delivery With Rapidly Dissolving Polymer Microneedles", Adv. Mater., 20:933-938 (2008).

Sun, T., et al., "Activation of Multiple Proto-oncogenic Tyrosine Kinases in Breast Cancer via Loss of the PTPN12 Phosphatase", Cell, 144:703-718 (2011).

Tang, C., et al., "Adhesion and Endothelialization of Endothelial Cells on the Surface of Endovascular Stents by the Novel Rotational Culture of Cells," Applied Surface Science, 255:315-319 (2008).

Tang, M.X., et al., "In Vitro Gene Delivery by Degraded Polyamidoamine Dendrimers", *Bioconjugate Chem.*, 7:703-714 (1996).

Taratula, O., et al., "Surface-Engineered Targeted PPI Dendrimer for Efficient Intracellular and Intratumoral siRNA Delivery", J. Control. Release, 140:284-293 (2009).

Tetko, I.V., et al., "Virtual Computational Chemistry Laboratory-design and description," *Computer-Aided Mol. Des.*, 19: 453-463 (2005).

Thompson, M.T., et al., "Biochemical Functionalization of Polymeric Cell Substrata Can Alter Mechanical Compliance", *Biomacromolecules*,7(6):1990-5 (2006).

Thompson, M.T., et al., "Tuning Compliance of Nanoscale Polyelectrolyte Multilayers to Modulate Cell Adhesion", *Biomaterials*, 26(34):6836-45 (2005).

Tijsterman, M., et al., "The Genetics of RNA Silencing", Annu Rev. Genet., 36:489-519 (2002).

Toniolo, C. et al., "II. Circular Dichroism Study of the Three Main Components of Clupeine", *Biochim Biophys Act.*, 576(2):429-39 (1979).

Trubetskoy, V.S., et al., "Layer-By-Layer Deposition of Oppositely Charged Polyelectrolytes on the Surface of Condensed DNA Particles", Nucleic Acids Res., 27:3090-3095 (1999).

Turner, J.G., et al., "ABCG2 Expression, Function, and Promoter Methylation in Human Multiple Myeloma", Blood, 108(12):3881-3889 (2006).

Uhrich, K.E., et al., "Polymeric Systems for Controlled Drug Release," *Chem. Rev.*, 99:3181-3198 (1999).

Uhrich, K., "Hyperbranched Polymers for Drug Delivery" Trends Polym. Sci.,5: 388-393 (1997).

van de Wetering, P., et al., "Structure-Activity Relationships of Water-Soluble Cationic Methacrylate/Methacrylamide Polymers for Non Viral Gene Delivery", *Bioconjugate Chem.*, 10: 589-597 (1999).

Vázquez, C.P., et al., "Variation of Polyelectrolyte Film Stiffness by Photo-Cross-Linking: A New Way to Control Cell Adhesion", *Langmuir*, 25(6):3556-63 (2009).

Vittal, R., et al., "Surfactant Promoted Enhancement on Electrochemical and Electrochromic Properties of Films of Prussian Blue and Its Analogs," Journal of the Electrochmical Socitey, 146(2):786-793 (1999).

Vo, T.N., et al., "Strategies for Controlled Delivery of Growth Factors and Cells for Bone Regeneration", Adv Drug Deliv Rev, 64(12): 1292-1309 (2012).

Wang D., et al., "Synthesis and Evaluation of Water-Soluble Polymeric Bone-Targeted Drug Delivery Systems," Bioconjugate Chemistry, 14(5): 853-859 (2003).

Wang, J., et al., "A Novel Biodegradable Gene Carrier Based on Polyphoophoester," J. Am. Chem. Soc., 123:9480-9481 (2001).

Wang, P.M., et al., "Precise Microinjection into Skin Using Hollow Microneedles", J. Invest. Dermatol., 126:1080-1087 (2006).

Warner, T.D., et al., "Nonsteroid Drug Selectives for Cyclo-Oxygenase-1 Rather Than Cyclo-Oxygenase-2 are associated with Human Gastrointestinal Toxicity: A full in vitro Analysis," *Proceedings of the National Academy of Sciences of the USA*, 96:7563-7568 (1999).

Watts, N.B. and Diab, D.L., "Long-Term Use of Bisphosphonates in Osteoporosis", J Clin Endocr Metab, 95(4): 1555-1565 (2010).

Wick, D.A., et al., "Profound CD8+ T Cell Immunity Elicited by Sequential Daily Immunization With Exogenous Antigen Plus the TLR3 Agonist Poly(I:C)", Vaccine, 29:984-993 (2011).

Wikipedia, Heparin, accessed Oct. 15, 2014, pp. 1-18.

Wiley and Sons, Lysozyme: Substrate Structure, accessed Oct. 15, 2014, p. 1.

Will, J., et al., "Porous Ceramic Bone Scaffolds for Vascularized Bone Tissue Regeneration", Journal of Materials Science, 19(8): 2781-2790 (2008).

Winer, E.P. and Mayer, E.L., "Optimizing Treatment of "Triple-Negative" Breast Cancer", SABCS 2007: Improving Outcomes in Advanced and Meta-static Breast Cancer, 8 pages, (2007), http://www.medscape.org/viewarticle/569483.

Woeblecke, H., et al., "Reversal of Breast Cancer Resistance Protein-Mediated Drug Resistance by Tryprostatin A", International Journal of Cancer, 107:721-728 (2003).

Wood, K.S., et al., "Controlling Interlayer Diffusion to Achieve Sustained, Multiagent Delivery from Layer-by-Layer Thin Films," *Proceedings of the National Academy of Sciences of the United States of America*, 103(27):10207-10212 (2006).

Wood, K.S., et al., "Tunable Drug Release From Hydrolytically Degradable Layer-By-Layer Thin Films", *Langmuir*, 21(4):1603-9 (2005).

Wood, E.R. et al., "A Unique Structure for Epidermal Growth Factor Receptor Bound to GW572016 (Lapatinib): Relationships among Protein Conformation, Inhibitor Off-Rate, and Receptor Activity in Tumor Cells", *Cancer Research*, 64:6652-6659 (2004).

Woodruff, M.A., et al., "Bone Tissue Engineering: From Bench to Bedside", Materials Today, 15(10): 430-435 (2012).

Yang, J. and Duerksen-Hughes, P., "A New Approach to Identifying Genotoxic Carcinogens: p53 Induction as an Indicator ofGenotoxic Damage", *Carcinogenesis*, 19: P1117-P1125 (1998).

Yoon, C.-H., et al., "Activation of p38 Mitogen-Activated Protein Kinase is Required for Death Receptor-Independent Caspase-8 Activation and Cell Death in Response to Sphingosine", Molecular Cancer Research, 7(3):361-370 (2009).

Zauner, W., et al., "Polylysine-Based Transfection Systems Utilizing Receptor-Mediated Delivery", *Adv. Drug. Del. Rev.*,30: 97-113 (1998).

Zhang, J., et al., "Multilayered Thin Films that Sustain the Release of Functional DNA under Physiological Conditions," Langmuir, 20(19): 8015-8021 (2004).

Zhang, J., et al., "Structure/Property Relationships in Erodible Multilayered Films: Influence of Polycation Structure on Erosion Profiles and the Release of Anionic Polyelectrolytes", Langmuir, 22:239-245 (2006).

Zhang, Y., et al., "In Vitro Observations of Self-Assembled ECM-Mimetic Bioceramic Nanorescrvoir Delivering rFN/CDH to Modulate Osteogenesis", Biomaterials, 33(30): 7468-7477 (2012).

Zheng, H., et al., "Controlling Cell Attachment Selectively Onto Biological Polymer-Colloid Templates Using Polymer-On-Polymer Stamping", *Langmuir*, 20(17):7215-22 (2004).

Zhou, Q.X. and Kohn, J., "Preparation of Poly(L-serine ester): A Structural Analogue of Conventional Poly(L-serine)", *Macromolecules*,23:3399-3406 (1990).

European Search Report of 08771046.3, entitled "Self Assembled Films for Protein and Drug Delivery Applications," dated Oct. 22, 2012, 4 pages.

International Preliminary Report on Patentability for PCT/US08/66948, entitled: Self Assembled Films for Protein and Drug Delivery Applications: Date of Issuance: Dec. 17, 2009.

International Search Report for PCT/US08/66948: entitled: Self Assembled Films for Protein and Drug Delivery Applications: Date of Mailing: Aug. 29, 2008. (incorrectly cited as Aug. 23, 2008).

(56) References Cited

OTHER PUBLICATIONS

International Preliminary Examination Report for PCT/US2002/34191, entitled: Methods of Making Decomposable Thin Films of Polyelectrolytes and Uses Thereof, Date of completion of report: Sep. 11, 2003.
International Search Report for PCT/US2002/34191, entitled: Methods of Making Decomposable Thin Films of Polyelectrolytes and Uses Thereof, Date mailed: Jan. 17, 2003.
International Search Report for PCT/US2006/004295, entitled: Electrochemically Degradable Layer-By-Layer Thin Films, Date of Issuance: Oct. 2, 2006.
International Preliminary Report on Patentability for PCT/US2006/004295, entitled: Electrochemically Degradable Layer-By-Layer Thin Films, Date of Issuance: Aug. 7, 2007.
International Search Report for PCT/US2007/069937, entitled: Methods of Making Decomposable Thin Films of Polyelectrolytes and Uses Thereof, Date of mailing: Aug. 13, 2008.
International Preliminary Report on Patentability for PCT/US2007/069937, entitled: Methods of Making Decomposable Thin Films of Polyelectrolytes and Uses Thereof, Date of Issuance: Dec. 3, 2008.
International Preliminary Report on Patentability for PCT/US2007/69964, entitled: Methods of Making Decomposable Thin Films of Polyelectrolytes and Uses Thereof, Date of Issuance: Dec. 3, 2008.
International Search Report and Written Opinion for PCT/US2007/69964, entitled: Methods of Making Decomposable Thin Films of Polyelectrolytes and Uses Thereof, Date of Issuance: Oct. 29, 2007.
International Preliminary Report on Patentability and Written Opinion for PCT/US2009/054011, entitled: Controlled Delivery of Bioactive Agents From Decomposable Films: Date of issuance: Feb. 22, 2011.
International Search Report for PCT/US2009/054011, entitled: Controlled Delivery of Bioactive Agents From Decomposable Films: Date of mailing: Nov. 24, 2010.
International Preliminary Report on Patentability for PCT/US2011/035057, entitled: Drug Deliver Coating and Devices, Date of issuance: Nov. 6, 2012.
International Search Report for PCT/US2011/035057, entitled: Drug Deliver Coating and Devices, Date of mailing: Feb. 8, 2012.
International Preliminary Report on Patentability and Written Opinion for PCT/US2012/035689, entitled: Coating Compositions, Methods and Coated Devices, Date of Issuance: Oct. 29, 2013.
International Search Report for PCT/US2012/035689, entitled: Coating Compositions, Methods and Coated Devices, Date of Mailing: Jul. 31, 2012.
International Preliminary Report on Patentability for PCT/US2012/035692, entitled: Coating Compositions, Methods and Coated Devices, Date of Issuance: Oct. 29, 2013.
International Search Report for PCT/US2012/35692, entitled: Coating Compositions, Methods and Coated Devices, Date of Mailing: Oct. 5, 2012.
International Search Report for PCT/US2013/066980, entitled: Devices and Methods for Layer-by-Layer Assembly, Date of Mailing: Apr. 30, 2014.
International Search Report for PCT/US2013/37868, entitled: Compositions and Methods of Treatment of Drug Resistant Cancers, Date of Mailing: Sep. 6, 2013.
International Search Report for PCT/US2013/37869, entitled: Stable Layer-By-Layer Coated Particles, Date of Mailing: Sep. 13, 2013.
International Search Report for PCT/US2014/018284, entitled:Nucleic Acid Particles, Methods and Use Thereof, Date of mailing: Jul. 30, 2014.
Written Opinion PCT/US2014/018284, entitled:Nucleic Acid Particles, Methods and Use Thereof, Date of mailing: Jul. 30, 2014.
International Search Report for PCT/US2014/022107, entitled: Compositions and Methods for Nucleic Acid Delivery, Date of mailing: Jun. 5, 2014.
Written Opinion for PCT/US2014/022107, entitled: Compositions and Methods for Nucleic Acid Delivery, Date of mailing: Jun. 5, 2014.
International Search Report and the Written Opinion for PCT/US2013/022430, entitled: Compositions and Methods for Coating, Date of mailing: May 15, 2013.
International Preliminary Report on patentability for PCT/US2013/022430, entitled: Compositions and Methods for Coating, Date of mailing: Jul. 22, 2014.
International Preliminary Report on Patentability for PCT/US2013/37869, entitled: Stable Layer-By-Layer Coated Particles, Date of Mailing: Nov. 6, 2014.
International Preliminary Report on Patentability for PCT/US2013/037868, entitled: Compositions and Methods of Treatment of Drug Resistant Cancers, Date of Mailing: Nov. 20, 2014.
International Search Report for PCT/US2014/057496, entitled: Biodegradable Layer-by-Layer (LbL) Films for Cell Capture and Release, Date of mailing: Jan. 8, 2015.
International Preliminary Report on Patentability for PCT/US2013/064530, entitled: Multilayer Compositions, Coated Devices and Use Thereof, Date of Mailing: Apr. 8, 2014.
Office Action for U.S. Appl. No. 13/115,107, entitled: "Multilayer Coating Compositions, Coated Substrates and Methods Thereof", Dated: Apr. 17, 2014.
Final Office Action for U.S. Appl. No. 13/115,107, entitled: "Multilayer Coating Compositions, Coated Substrates and Methods Thereof", Dated: Apr. 17, 2014.
Final Office Action for U.S. Appl. No. 12/542,267, entitled: "Controlled Delivery of Bioactive Agents From Decomposable Films", Dated: Mar. 11, 2015.
Office Action for U.S. Appl. No. 12/542,267, entitled: "Controlled Delivery of Bioactive Agents From Decomposable Films", Dated: Mar. 31, 2014.
Office Action for U.S. Appl. No. 12/542,267, entitled: "Controlled Delivery of Bioactive Agents From Decomposable Films", Dated: Jun. 7, 2013.
Office Action for U.S. Appl. No. 12/542,267, entitled: "Controlled Delivery of Bioactive Agents From Decomposable Films", Dated: Aug. 17, 2012.
Office Action for U.S. Appl. No. 12/139,151, entitled: "Self Assembled Films for Protein and Drug Delivery Applications", Dated: Jun. 11, 2014.
Office Action for U.S. Appl. No. 12/139,151, entitled: "Self Assembled Films for Protein and Drug Delivery Applications", Dated: Jun. 20, 2012.
Office Action for U.S. Appl. No. 12/139,151, entitled: "Self Assembled Films for Protein and Drug Delivery Applications", Dated: Sep. 22, 2011.
Office Action for U.S. Appl. No. 11/459,979, entitled: "Methods of Making Decomposable Thin Films of Polyelectrolytes and Uses Thereof", Dated: Jul. 23, 2010.
Office Action for U.S. Appl. No. 11/459,979, entitled: "Methods of Making Decomposable Thin Films of Polyelectrolytes and Uses Thereof", Dated: Oct. 29, 2009.
Office Action for U.S. Appl. No. 11/815,718, entitled: "Electrochemically Degradable Layer-By-Layer Thin Films", Dated: Mar. 27, 2014.
Office Action for U.S. Appl. No. 11/815,718, entitled: "Electrochemically Degradable Layer-By-Layer Thin Films", Dated: Nov. 27, 2012.
Office Action for U.S. Appl. No. 11/815,718, entitled: "Electrochemically Degradable Layer-By-Layer Thin Films", Dated: Mar. 26, 2012.
Office Action for U.S. Appl. No. 10/280,268, entitled: "Methods of Making Decomposable Thin Films of Polyelectrolytes and Uses Thereofs", Dated: Nov. 2, 2004.
Office Action for U.S. Appl. No. 10/280,268, entitled: "Methods of Making Decomposable Thin Films of Polyelectrolytes and Uses Thereofs", Dated: Jul. 6, 2005.
Office Action for U.S. Appl. No. 10/280,268, entitled: "Methods of Making Decomposable Thin Films of Polyelectrolytes and Uses Thereofs", Dated: Jun. 29, 2006.
Office Action for U.S. Appl. No. 13/459,066, entitled: "Coating Compositions, Methods and Coated Devices", Dated: Oct. 15, 2014.

(56) References Cited

OTHER PUBLICATIONS

Office Action for U.S. Appl. No. 13/459,069 entitled: "Coating Compositions, Methods and Coated Devices", Dated: Oct. 23, 2014.
Office Action for U.S. Appl. No. 13/869,015 entitled: "Stable Layer-By-Layer Coated Particles", Dated: Nov. 21, 2014.
Office Action for U.S. Appl. No. 13/695,836 entitled: "Drug Delivery Coating and Devices", Dated: Nov. 28, 2014.
Office Action for U.S. Appl. No. 13/746,902 entitled: "Compositions and Methods for Coating," Dated: Jan. 2, 2015.
Office Action for U.S. Appl. No. 14/190,983, "Nucleic Acid Particles, Methods and Use Thereof", date of mailing Jan. 29, 2015.
Office Action for U.S. Appl. No. 13/869,012, "Compositions and Methods of Treatment of Drug Resistant Cancers", date of mailing Apr. 7, 2015.
International Preliminary Report on Patentability for PCT/US2013/066980, entitled: Devices and Methods for Layer-by-Layer Assembly, Date of Mailing: May 7, 2015.
Final Office Action for U.S. Appl. No. 13/115,107, entitled: "Multilayer Coating Compositions, Coated Substrates and Methods Thereof", Dated: Jan. 28, 2015.

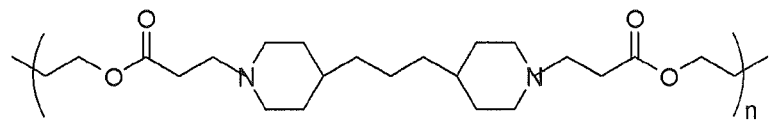
Polymer 1 (Poly1)
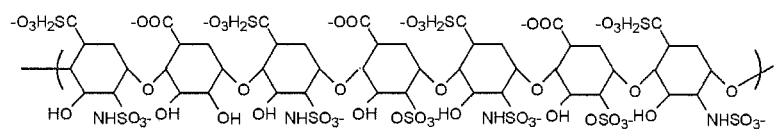
Heparin Sulfate
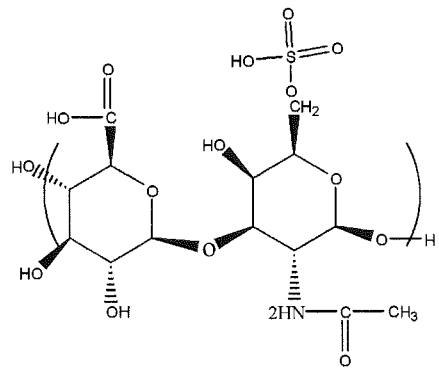
Chondroitin Sulfate
Polymer 2 (Poly2)
FIGURE 1

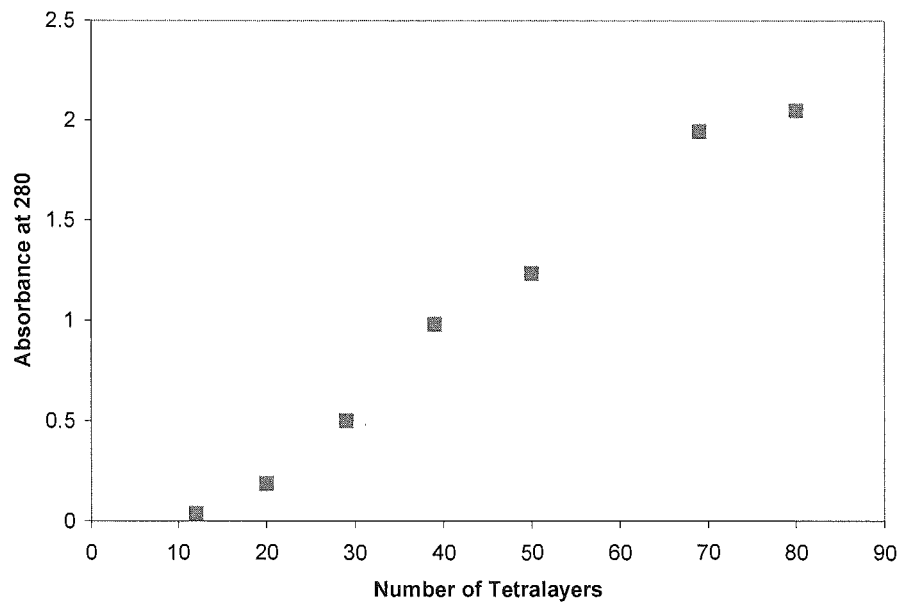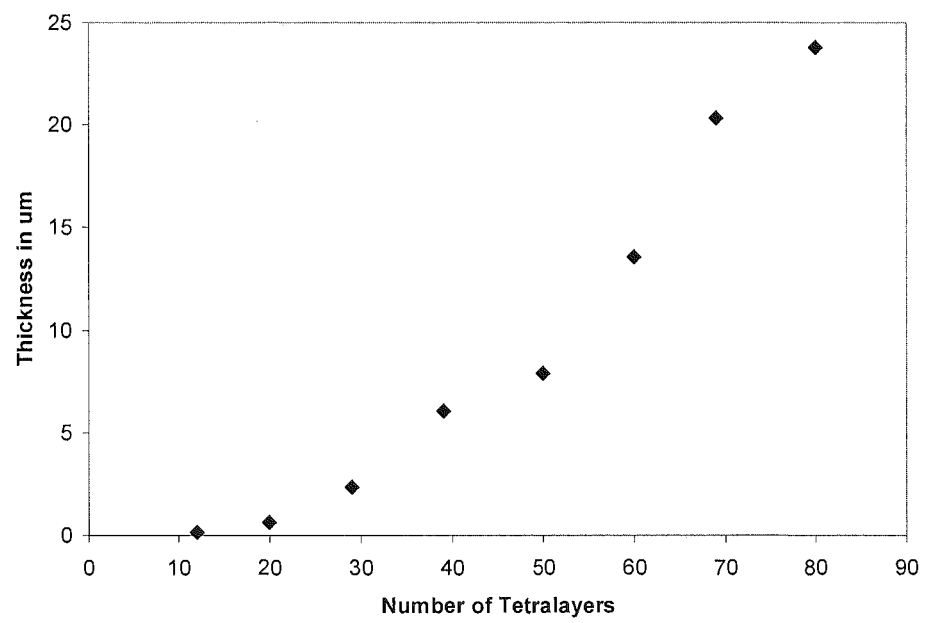
FIGURES 3A-B

C
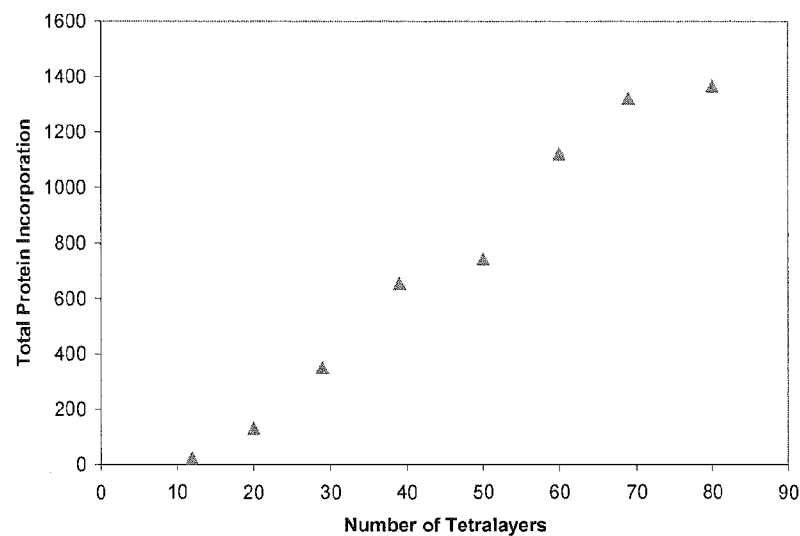
D
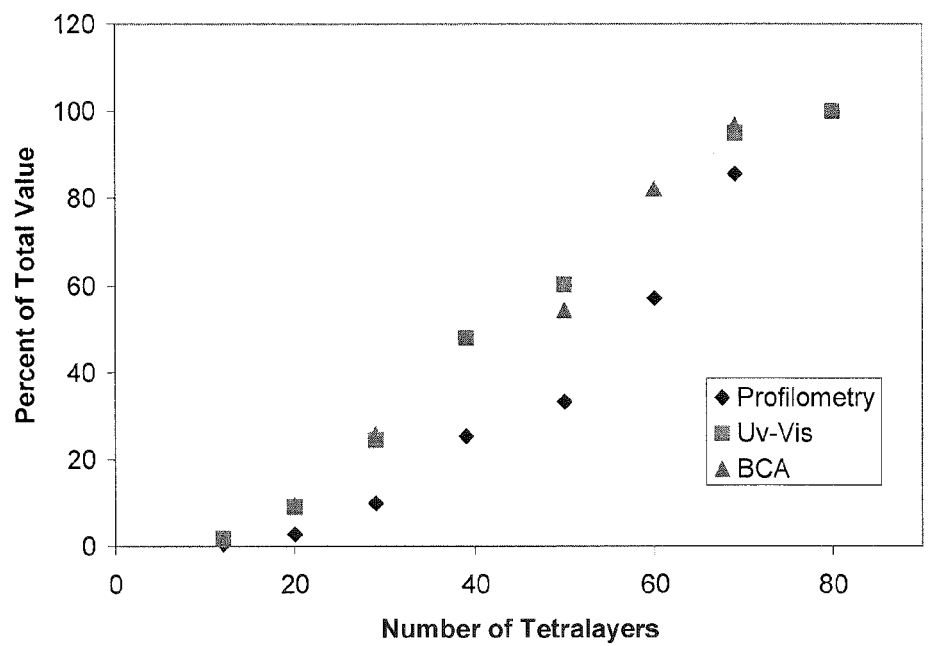
FIGURES 3C-D

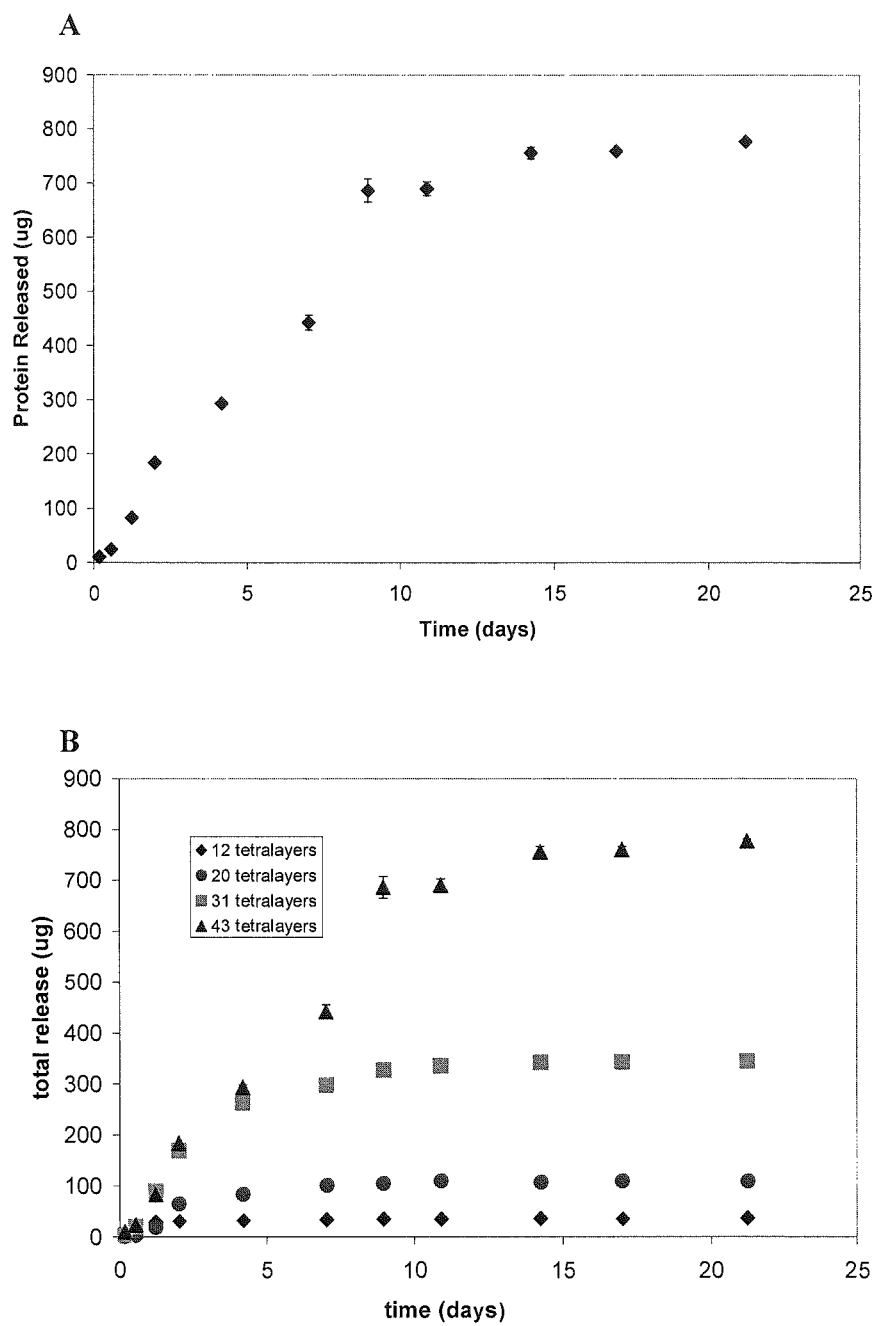
FIGURES 4A-B

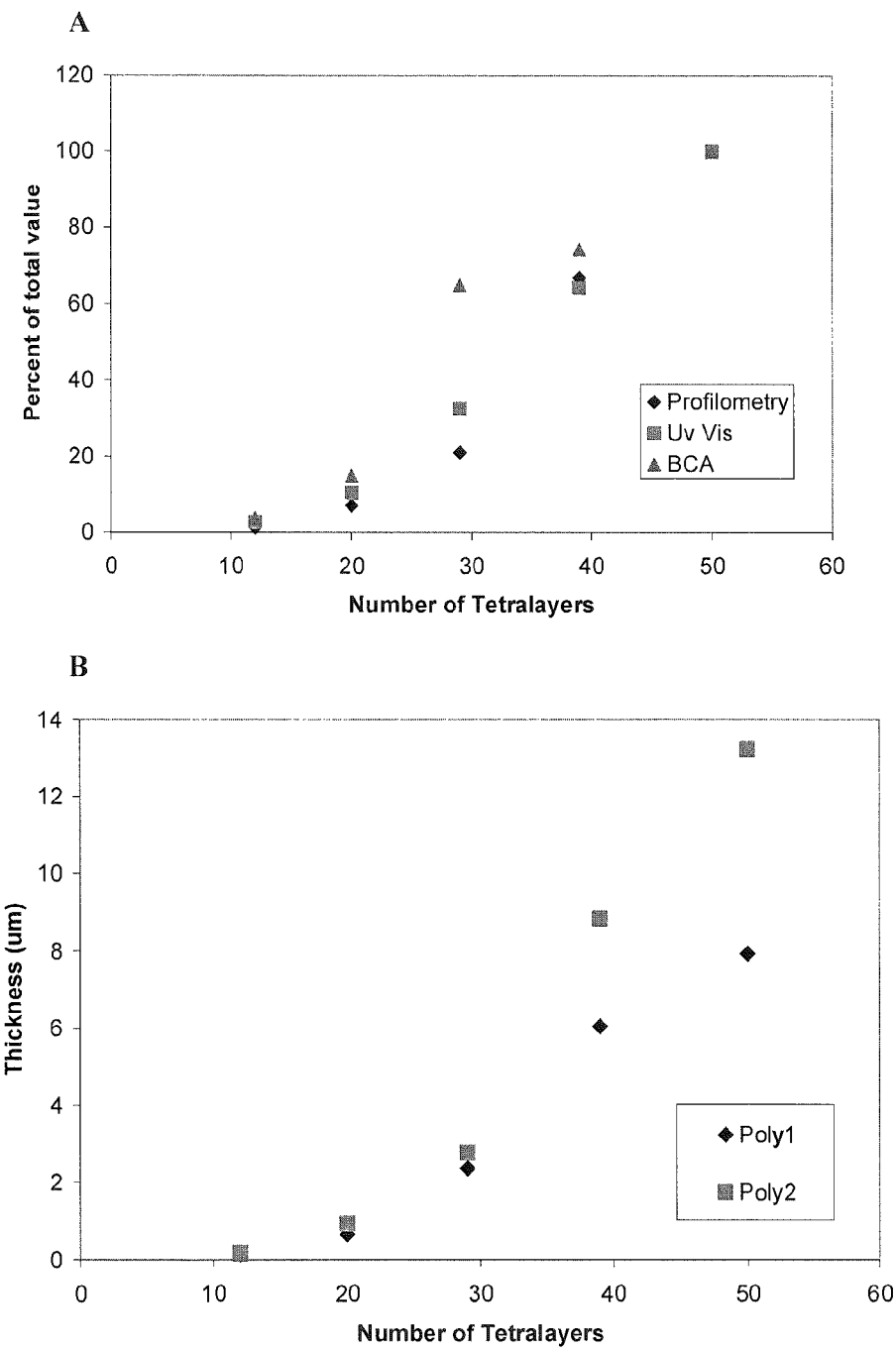
FIGURES 5A-B

SELF ASSEMBLED FILMS FOR PROTEIN AND DRUG DELIVERY APPLICATIONS

RELATED APPLICATIONS

This application is a divisional of U.S. application Ser. No. 12/139,151, filed Jun. 13, 2008, which claims priority to and claims benefit of U.S. Provisional Application No. 60/943,983 filed Jun. 14, 2007, the entire contents of which are herein incorporated by reference.

GOVERNMENT FUNDING

This invention was made with Government support under Grant No. R01 AG029601 awarded by the National Institutes of Health. The Government has certain rights in the invention.

BACKGROUND

Many proteins are potentially useful in therapeutic drug applications. Nevertheless, controlled delivery of proteins remains a challenge, due in part to the fragile nature of some proteins (such as enzyme polypeptides) and the ability of proteins to diffuse. Sustained delivery of proteins while maintaining function is particularly desirable.

Layer-by-layer (LbL) absorption of oppositely charged polyelectrolytes on substrates can be used to fabricate thin multi-layer films for drug development. Nevertheless, LbL-based methods of delivering drugs were traditionally based on the formation of uniform films from which drug escapes via diffusion. Such diffusion-based release limits or eliminates the opportunity for controlled sequential delivery of drugs released from the surface to the surrounding medium. With such films, a typical diffusive, nonlinear drug release pattern is observed, and rarely is diffusion-controlled release from LbL films sustained for more than a few hours.

Because release time is impacted by the affinity of the drug for water, it is directly related to the hydrophobic nature of the drug, rather than an externally controlled parameter. Thus, releasing drugs by diffusion is not a useful strategy for all hydrophilic drugs, such as proteins. Other methods allow encapsulation of proteins within a shell of LbL coats for release under significant pH (pH 8 or higher) or ionic strength changes, nevertheless, this is impractical for many medical applications, as such large deviations from physiological conditions would be often deadly. Also, processing methods for such films typically involve harsh solvents, in addition to acidic byproducts of degradation, which may destroy the protein intended to be delivered.

SUMMARY

In various embodiments, the invention provided systems for controlled release of proteins while preserving protein function using LbL deposition to incorporate proteins into decomposable thin films.

In one aspect, the invention provides decomposable thin films for releasing proteins. Such decomposable thin films generally comprise a plurality of multilayer units comprising a first layer having a first charge and second layer having a second charge. At least a portion of the multilayers comprise a protein and decomposition of the thin film is characterized by sequential removal of at least a portion of the layers having the first charge and degradation of layers having the second charge, and by release of the protein from the corresponding layer. The decomposable thin film comprises at least one degradable polyelectrolyte layer, wherein the degradable polyelectrolyte is hydrolyzable. Erosion of the polyelectrolyte layer allows release of the protein.

In certain embodiments, the decomposable thin film comprises alternating cationic and anionic layers, and decomposition of the thin film is characterized by hydrolytic degradation of at least a portion of a layer (such as a cationic layer, an anionic layer, or both). In some embodiments of the invention, the decomposable thin film is comprised of tetralayer units, with each tetralayer having a structure such as, for example, (cationic degradable polymer/polyanion/cationic protein/polyanion). Other structures are also contemplated in the invention. The protein can be any of a number of proteins, for example, growth factors, clotting factors, enzyme polypeptides, etc.

In certain embodiments, proteins released from films of the invention can be released in a controlled manner, for example, with a linear release profile. Such films with linear release profiles may be amenable to therapeutic drug applications. Dosing and release kinetics may be altered by altering one or more characteristics such as, for example, the degradable polymer used in film construction, the number of multilayers comprising the film, and/or the type of additional materials (such as polyanions) that are used in the construction of the films. Additional film properties such as anticoagulant activity or providing matrix material for cell proliferation can be chosen through the polyanion used. Examples of polyanions that can be used in accordance with the invention include charged polysaccharides such as heparin and chondroitin.

The thin film can be adapted or shaped and/or deposited onto substrates having certain shapes. This may facilitate making such films amenable for drug applications, such as, for example, those in which the films would be implanted into a patient's body. For example, the film may be constructed as a hollow shell, or deposited onto substrates having various shapes.

In another aspect, the invention provides methods of releasing proteins using decomposable thin films of the invention.

In certain embodiments, films and methods provided in the invention allow protein release over a period of at least 34 days and/or up to 80-100% retention of function of protein released from such films.

DEFINITIONS

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe materials that do not elicit a substantial detrimental response in vivo.

"Biodegradable": As used herein, "biodegradable" polymers are polymers that degrade fully under physiological or endosomal conditions. In preferred embodiments, the polymers and biodegradation byproducts are biocompatible. Biodegradable polymers are not necessarily hydrolytically degradable and may require enzymatic action to fully degrade.

"Degradation": The phrase "degradation", as used herein, relates to the cleavage of a covalent polymer backbone. Full degradation of a polymer breaks the polymer down to monomeric species.

"Endosomal conditions": The phrase "endosomal conditions", as used herein, relates to the range of chemical (e.g., pH, ionic strength) and biochemical (e.g., enzyme concentrations) conditions likely to be encountered within endosomal vesicles. For most endosomal vesicles, the endosomal pH ranges from about 5.0 to 6.5.

"Hydrolytically degradable": As used herein, "hydrolytically degradable" polymers are polymers that degrade fully in the sole presence of water. In preferred embodiments, the polymers and hydrolytic degradation byproducts are biocompatible. As used herein, the term "non-hydrolytically degradable" refers to polymers that do not fully degrade in the sole presence of water.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polyelectrolyte" or "polyion": The terms "polyelectrolyte" or "polyion", as used herein, refer to a polymer which under some set of conditions (e.g., physiological conditions) has a net positive or negative charge. Polycations have a net positive charge and polyanions have a net negative charge. The net charge of a given polyelectrolyte or polyion may depend on the surrounding chemical conditions, e.g., on the pH.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. The phrase "enzyme polypeptide" refers to a polypeptide having enzymatic activity.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present invention.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

Acronyms

The following acronyms are used herein: "SPS" is poly (styrene sulfonate), "PAA" is poly(acrylic acid), "LPEI" is linear poly(ethylene imine), "PDAC" is poly(diallyl dimethyl ammonium chloride), "PAH" is poly(allylamine hydrochloride), and "PAZO" is the azobenzene functionalized polymer poly {1-[4-(3-carboxy-4-hydroxyphenylazo)benzensulfonamido]-1,2-ethanediyl}.

BRIEF DESCRIPTION OF THE FIGURES

FIG. 1 depicts chemical structures of certain polymers used in accordance with the invention. Shown are the structures for polymer 1 (Poly1), heparin sulfate, chondroitin sulfate, and polymer 2 (Poly2). Note that Poly1 and Poly2 differ only by two methylene units in the backbone.

FIGS. 3A-D show results from characterization studies of (Poly1/heparin/lysozyme/heparin) tetralayers. Films were characterized by UV-Vis spectroscopy, profilometry, and instant dissolution methods. The number of tetralayers is plotted against the signal recorded at the point of construction. (A): UV-Vs absorbance of films at 280 nm with signal correction at 320 nm. (B): Profilometry measurements of films. (C): Amounts of protein instantaneously release from films as measured by a BCA (bicinchoninic acid) assay. (D): Overlay of the three measurement techniques to compare curves, showing agreement of all three methods in detecting the characteristics of film buildup. Each signal value is taken as a percentage of the signal at 80 tetralayers.

FIGS. 4A-C show results indicating that release is affected by temperature of release and the number of tetralayers. Time in days is plotted against total amount of protein released in μg. (A): Replicate samples dipped with the architecture [(Poly1/heparin/lysozyme/heparin)$_{80}$] were released at room temperature and displayed a linear release curve. (B): Films with the architecture [(Poly1/heparin/lysozyme/heparin)$_{50}$] were released at 37° C. and displayed a continued linear release profile. (C): Films comprised of various numbers of tetralayers were released in PBS. Both the amount of protein incorporated and the time to total release are increased with increasing numbers of tetralayers.

FIGS. 5A-C show results of characterization studies of Poly2-containing films. (A): The number of (poly2/heparin/lysozyme/heparin) tetralayers is plotted against the signal recorded at that point of construction. Each signal value is taken as a percentage of the signal at 50 tetralayers. (B): Comparison of Poly1 and Poly2 buildup curves. The number of (PolyX/heparin/lysozyme/heparin) tetralayers is plotted versus the total thickness of the film as measured by profilometry. (C): When poly2 is layered in the architecture [(Poly2/heparin/lysozyme/heparin)$_{50}$] and protein is released at 37° C., release of over 34 days is achieved, showing the tenability of this system in response to desired characteristics.

DETAILED DESCRIPTION OF CERTAIN EMBODIMENTS

As mentioned above, the invention provides, in various embodiments, systems for releasing proteins (including those having therapeutic value) in a controlled manner, while retaining activity of the released protein. Control may be achieved over dose, release rate, and/or time span.

Decomposable Films

Decomposition of the thin films of the invention is characterized by the substantially sequential degradation of at least a portion of the polyelectrolyte layers that make up the thin films. The degradation may be at least partially hydrolytic, at least partially enzymatic, at least partially thermal, and/or at least partially photolytic. In some embodiments, the thin films are about 1 nm and about 100 μm thick, for example, between about 1 nm and about 100 nm thick, between about 100 nm and about 1 μm thick, between about 1 μm and about 10 μm thick, or between about 10 μm and about 100 μm thick.

Films are generally comprised of alternating layers of surface erodible polyelectrolytes (such as degradable polymers) and ionic proteins. The film may be comprised of multilayer units with alternating layers of opposite charge, such as alternating anionic and cationic layers. For example, a cationic polyelectrolyte may be layered next to an anionic protein layer, and the bilayer unit repeated to make the thin film. Alternatively, an anionic polyelectrolyte may be layered next to a cationic protein layer.

At least one of the layers in a multilayer unit includes a degradable polyelectrolyte. As an example, the film may be comprised of an at least partially degradable polycationic layer and a layer of anionic protein. The thin film may be exposed to a degrading medium (e.g., intracellular fluid), whereupon the polycationic layers degrade and the protein layers delaminate sequentially from the surface toward the substrate. Proteins are thus gradually and controllably released from the surface of the thin film.

It will be appreciated that the roles of the layers of the thin film can be reversed. In such embodiments, the polyanionic layers include a degradable polyanion and the polycationic layers may include, for example, a polycationic protein. Alternatively, both the polycationic and polyanionic layers may both include degradable polyelectrolytes.

Figure 2:
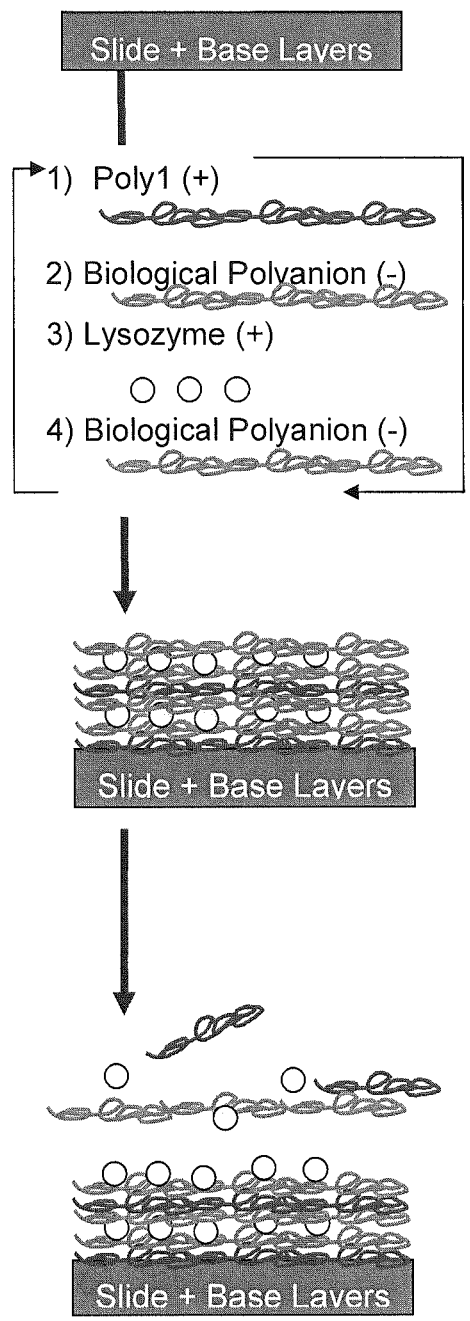
FIG. 2 illustrates a scheme that may be used to construct a film using a cationic polymer (Poly1) comprising a cationic protein (lysozyme). Layers of a biological polyanion are deposited between layers of Poly1 and layers of lysozyme onto a substrate such as a slide. Thus, the film is comprised of tetralayers, each tetralayer having the structure (Poly1/polyanion/lysozyme/polyanion.)

The invention also provides thin films in which the protein has the same charge as the chosen surface erodible polyelectrolyte. One such embodiment of the invention is illustrated in FIG. 2, in which a film is created by deposition of tetralayer units on a substrate via layer-by-layer assembly. The tetralayer units depicted in FIG. 2 comprise a layer of a cationic polymer (Poly1), a layer of a biologically active polyanion, a layer of the protein of interest (lysozyme in the example shown), and another layer of biologically active polyanion. Degradation of the film and controlled release of proteins form the surface of the thin film proceeds as described above, except that sequential removal of the intervening polyanionic layers also occurs.

Degradable polyelectrolytes and their degradation byproducts may be biocompatible so as to make the films amemable to use in vivo.

Assembly Methods

In certain embodiments, the LBL assembly of films may involve a series of dip coating steps in which the substrate is dipped in alternating polycationic and polyanionic solutions. Additionally or alternatively, it will be appreciated that deposition of alternating polycationic and polyanionic layers may also be achieved by spray coating, brush coating, roll coating, spin casting, or combinations of any of these techniques.

In certain embodiments, multiple layers of oppositely charged polymers are deposited on a charged surface from aqueous baths in a highly controllable process. Proteins can be incorporated into individual layers of the film, affording the opportunity for exquisite control of loading and release from the film. There are several advantages to this technique, including mild aqueous processing conditions (which may allow preservation of biomolecule function); nanometer-scale conformal coating of surfaces; and the flexibility to coat objects of any size, shape or surface chemistry, leading to versatility in design options.

Substrates for Constructing Films

A variety of materials can be used as substrates of the present invention such as, but not limited to, metals, e.g., gold, silver, platinum, and aluminum; metal-coated materials; metal oxides; plastics; ceramics; silicon; glasses; mica; graphite; hydrogels; and polymers such as polyamides, polyphosphazenes, polypropylfumarates, polyethers, polyacetals, polycyanoacrylates, polyurethanes, polycarbonates, polyanhydrides, polyorthoesters, polyhydroxyacids, polyacrylates, ethylene vinyl acetate polymers and other cellulose acetates, polystyrenes, poly(vinyl chloride), poly(vinyl fluoride), poly(vinyl imidazole), poly(vinyl alcohol), poly(ethylene terephthalate), polyesters, polyureas, polypropylene, polymethacrylate, polyethylene, poly(ethylene oxide)s and chlorosulphonated polyolefins; and combinations thereof. For example, a substrate of one material may be coated with a second material, or two materials may be combined to form a composite.

It will be appreciated that materials with an inherently charged surface are particularly attractive substrates for LBL assembly of a thin film. Alternatively, a range of methods are known in the art that can be used to charge the surface of a material, including but not limited to plasma processing, corona processing, flame processing, and chemical processing, e.g., etching, micro-contact printing, and chemical modification. For example, plastics can be used as substrates, particularly if they have been chemically modified to present polar or charged functional groups on the surface. Additionally or alternatively, substrates can be primed with specific polyelectrolyte bilayers such as, but not limited to, LPEI/SPS, PDAC/SPS, PAH/SPS, LPEI/PAA, PDAC/PAA, and PAH/PAA bilayers, that form readily on weakly charged surfaces and occasionally on neutral surfaces. It will be appreciated that primer layers provide a uniform surface layer for further LBL assembly and are therefore particularly well suited to applications that require the deposition of a uniform thin film on a substrate that includes a range of materials on its surface, e.g., an implant (such as stent) or a complex tissue engineering construct.

The substrate geometry may be manipulated to deposit films having a variety of shapes. For example, films may be deposited on particles, tubes, or spheres to facilitate a more uniform release distribution. Films may be deposited on strands such as sutures to release factors such as analgesics or antibiotics at a surgical site; coiled strands may also serve as substrates. Alternatively, these films may be deposited onto capillary networks or tissue engineering constructs. For example, a thin film deposited on a three-dimensional tissue engineering construct may be used to attract cells to a newly implanted construct and then to promote specific metabolic or proliferative activity.

Methods of the invention may also be used to create three-dimensional microstructures. For example, the thin film may be deposited on a substrate that can be dissolved to leave a hollow shell of the thin film. Alternatively or additionally, multi-layers may be deposited on substrates having regions that are more and less degradable. Degradation of the degradable portions leaves a three-dimensional microstructure. In a first step, the surface of a substrate is divided into regions in which LBL deposition of an inventive thin film is more or less favorable. In one embodiment, a pattern of self-assembled monolayers (SAMs) is deposited on a substrate surface by microcontact printing (see, for example, U.S. Pat. No. 5,512,131 to Kumar et al., see also Kumar et al., *Langmuir* 10:1498, 1994; Jiang and Hammond, *Langmuir*, 16:8501, 2000; Clark et al., *Supramolecular Science* 4:141, 1997; and Hammond and Whitesides, *Macromolecules* 28:7569, 1995). In some embodiments, the substrate surface is neutral and the exposed surface of the deposited SAMs is polar or ionic (i.e., charged). A variety of polymers with polar or ionic head groups are known in the art of self-assembled monolayers. In some embodiments, a uniform coating of a polymer is deposited on a substrate, and that coating is transformed into a patterned layer by means of photolithography. Other embodiments are also contemplated in which the substrate surface is selectively exposed to plasmas, various forms of electromagnetic radiation, or to electron beams. In yet other embodiments, the substrate may possess the desired surface characteristics by virtue of its inherent composition. For example, the substrate may be a composite in which different regions of the surface have differing compositions, and thus different affinities for the polyelectrolyte to be deposited.

In a second step, polyelectrolyte layers of alternating charge are deposited by LBL on receptive regions of the surface as described for a homogeneous surface above and selective regions in Jiang and Hammond, *Langmuir*, 16:8501, 2000; Clark et al., *Supramolecular Science* 4:141, 1997; and Hammond and Whitesides, *Macromolecules* 28:7569, 1995. The surface is subsequently flooded with a non-degradable polymer and placed in a medium wherein at least a portion of the polyelectrolyte layers degrade, thereby creating a three-dimensional "tunnel-like" structure that reflects the pattern on the original surface (see FIG. 9, step D). It will be appreciated that more complex microstructures could be created based on these simple principles (e.g., by depositing SAMs with different electrostatic character in different regions of a substrate surface and/or by iterative additions of subsequent structures above the deposited non-degradable polymer).

Degradable Polyelectrolytes

Any degradable polyelectrolyte can be used in a thin film of the present invention, including, but not limited to, hydrolytically degradable, biodegradable, thermally degradable, and photolytically degradable polyelectrolytes. Hydrolytically degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used in the present invention include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806, 621; 4,638,045 to Kohn; and U.S. Pat. No. 4,946,929 to d'Amore; see also Wang et al., J. Am. Chem. Soc. 123:9480, 2001; Lim et al., J. Am. Chem. Soc. 123:2460, 2001; Langer, Acc. Chem. Res. 33:94, 2000; Langer, J. Control Release 62:7, 1999; and Uhrich et al., Chem. Rev. 99:3181, 1999. Of course, co-polymers, mixtures, and adducts of these polymers may also be employed.

The anionic polyelectrolytes may be degradable polymers with anionic groups distributed along the polymer backbone. The anionic groups, which may include carboxylate, sulfonate, sulphate, phosphate, nitrate, or other negatively charged or ionizable groupings, may be disposed upon groups pendant from the backbone or may be incorporated in the backbone itself. The cationic polyelectrolytes may be degradable polymers with cationic groups distributed along the polymer backbone. The cationic groups, which may include protonated amine, quaternary ammonium or phosphonium-derived functions or other positively charged or ionizable groups, may be disposed in side groups pendant from the backbone, may be attached to the backbone directly, or can be incorporated in the backbone itself.

For example, a range of hydrolytically degradable amine containing polyesters bearing cationic side chains have recently been developed (Putnam et al. Macromolecules 32:3658-3662, 1999; Barrera et al. J. Am. Chem. Soc. 115: 11010-11011, 1993; Kwon et al. Macromolecules 22:3250-3255, 1989; Lim et al. J. Am. Chem. Soc. 121:5633-5639, 1999; Zhou et al. Macromolecules 23:3399-3406, 1990; each of which is incorporated herein by reference). Examples of these polyesters include poly(L-lactide-co-L-lysine) (Barrera et al. J. Am. Chem. Soc. 115:11010-11011, 1993; incorporated herein by reference), poly(serine ester) (Zhou et al. Macromolecules 23:3399-3406, 1990; which is incorporated herein by reference), poly(4-hydroxy-L-proline ester) (Putnam et al. Macromolecules 32:3658-3662, 1999.; Lim et al. J. Am. Chem. Soc. 121:5633-5639, 1999; each of which is incorporated herein by reference), and more recently, poly[α-(4-aminobutyl)-L-glycolic acid].

In addition, poly(β-amino ester)s, prepared from the conjugate addition of primary or secondary amines to diacrylates, are suitable for use with the invention. Typically, poly(β-amino ester)s have one or more tertiary amines in the backbone of the polymer, preferably one or two per repeating backbone unit. Alternatively, a co-polymer may be used in which one of the components is a poly(β-amino ester). Poly (β-amino ester)s are described in U.S. Ser. No. 09/969,431, filed Oct. 2, 2001, entitled "Biodegradable poly(β-amino esters) and uses thereof" and Lynn et al., J. Am. Chem. Soc. 122:10761-10768, 2000, the entire contents of both of which are incorporated herein by reference.

Exemplary poly(β-amino ester)s include

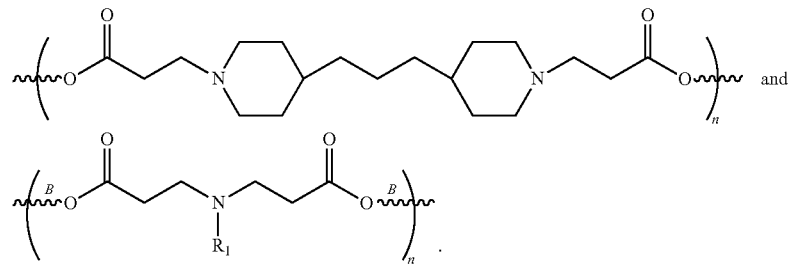

Exemplary R groups include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups.

Exemplary linker groups A and B include carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. The polymer may include, for example, between 5 and 10,000 repeat units.

In some embodiments of the invention, the poly(β-amino ester) are Poly1 and/or Poly2 (whose structures are shown in FIG. 1).

Alternatively or additionally, zwitterionic polyelectrolytes may be used. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, a film may be deposited by LBL deposition using dip coating in solutions of a first pH at which one layer is anionic and a second layer is cationic. If the film is put into a solution having a second different pH, then the first layer may be rendered cationic while the second layer is rendered anionic, thereby changing the charges on those layers.

Figure 4C:
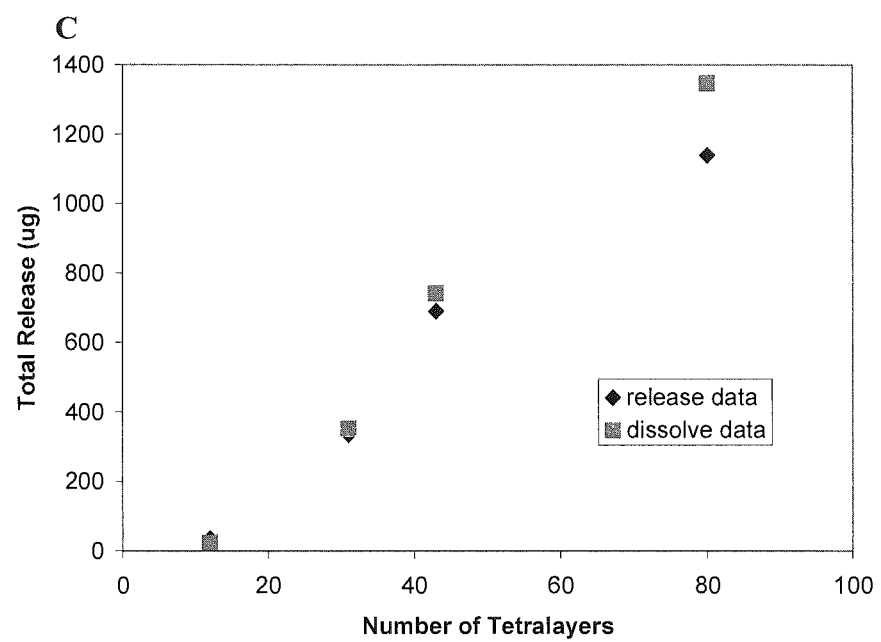

The composition of the polyanionic and polycationic layers can be fine-tuned to adjust the degradation rate of each layer within the film. For example, the degradation rate of hydrolytically degradable polyelectrolyte layers can be decreased by associating hydrophobic polymers such as hydrocarbons and lipids with one or more of the layers. Alternatively, the polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions. In other embodiments, the polyanionic and/or polycationic layers may include a mixture of degradable and non-degradable polyelectrolytes. Any non-degradable polyelectrolyte can be used with the present invention. Exemplary non-degradable polyelectrolytes that could be used in thin films are shown in FIG. 4 and include poly(styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

Alternatively or additionally, the degradation rate may be fine-tuned by associating or mixing non-biodegradable, yet biocompatible polymers (polyionic or non-polyionic) with one or more of the polyanionic and/or polycationic layers. Suitable non-biodegradable, yet biocompatible polymers are well known in the art and include polystyrenes, certain polyesters, non-biodegradable polyurethanes, polyureas, poly(ethylene vinyl acetate), polypropylene, polymethacrylate, polyethylene, polycarbonates, and poly(ethylene oxide)s.

Proteins

Proteins that can be incorporated into films of the present invention include, but are not limited to, growth factors, clotting factors, and/or enzyme polypeptides. It may be desirable, for example, to release growth factors for tissue engineering purposes, and/or for implantable medical devices. Growth factors that may be released using films provided by the present invention include, but are not limited to, vascular endothelian growth factor (VEGF), bone morphogenic protein 2 (BMP-2), bone morphogenic protein 4 (BMP-4), and basic fibroblast growth factor.

Release of clotting factors (also known as coagulation factors) may promote desired biological processes such as wound healing in certain embodiments of the invention. The clotting factor may be, but is not limited to, factor I (fibrinogen), factor VII (prothrombin), factor III (tissue thromboplastin), factor V (proaccelerin), factor VII (proconvertin), factor VIII (antihemophilic factor), factor IX (plasma thromboplastin component), factor X (thrombokinase), factor XI (plasma thromboplastin antecedent), factor XII (Hageman factor), and factor XIII (fibrin stabilizing factor).

Enzymes other than some of the clotting factors listed above may also be released using films and methods of the present invention. For example, lysozyme lyse bacteria and may have therapeutic uses. Lysozyme is used as a model enzyme in Examples 3-8 in the present application. Example 8 demonstrates that enzyme released from films of the invention retain catalytic activity.

More than one protein can be released from a single film. For example, films may be constructed so as to have multiple layers of proteins (each layer containing different proteins), and/or such that the "protein layer" in each multilayer unit comprises more than one protein. This may be useful in applications, for example, that require or would benefit from release of more than one growth factor.

Polyions

Polyionic layers may be used in film construction and placed between protein layers and polyelectrolyte layers having the same charge. As discussed above, for example, in some embodiments, films comprise tetralayer units having the structure (degradable cationic polyelectrolyte/polyanion/cationic protein/polyanion). (Structures with reversed charge schemes, e.g., comprising anionic polyelectrolytes, polycations, and anionic proteins, may also be possible with the present invention.)

Polyions used in accordance with the invention are generally biologically derived, though they need not be. Polyions that may be used in accordance with the invention include charged polysaccharides. This include glycosaminoglycans such as heparin, chondroitin, dermatan, hyaluronic acid, etc. (Some of these terms for glycoasminoglycans are often used interchangeably with the name of the sulfate form, e.g., heparan sulfate, chondroitin sulfate, etc. It is intended that such sulfate forms are included among the list of polyions that may be used in accordance with the invention. Similarly, other derivatives or forms of such polysaccharides may be incorporated into films.)

In some embodiments, polyions also add characteristics to the film that are useful for medical applications. For example, heparin activates antithrombin III, which blocks thrombin activity, and therefore reduces clotting. Anti-clotting properties may be desirable for a delivery device or implant coating, as clotting as a serious concern with any device that may be put into contact with the bloodstream (i.e., stents). Failure to address this concern may lead myocardial infarction, stroke, or ischemia of other vital organs.

In some applications, anticoagulation would be problematic (for example, at a wound site) and other characteristics would be desirable. For example, it may be desired to speed integration of an implanted device into surrounding host tissue. Providing an extracellular matrix-like environment that encourages cell proliferation may facilitate integration. In such cases, a polyion such as chondroitin (a native extracellular matrix component with anti-inflammatory properties) could be used.

Dose and Release Characteristics

As mentioned above, certain characteristics of degradable thin films of the invention may be modulated to achieve desired protein doses and/or release kinetics. Doses may be modulated, for example, by changing the number of multilayer units that make up the film, the type of degradable polyelectrolyte used, the type of polyion (if any) used, and/or concentrations of protein solutions used during construction of the films. Similarly, release kinetics (both rate of release and duration of protein release) may be modulated by changing any or a combination of the aforementioned factors.

Methods

Also provided in the invention are methods of releasing a protein from a thin film of the invention. Such methods generally comprise steps of providing a decomposable thin film of the invention and placing the thin film in a medium in which at least a portion of the thin film decomposes via the substantially sequential removal of at least a portion of the layers having the first charge and degradation of layers having the second charge. The medium can be, for example, provided from in vivo environment such as a subject's body. In some embodiments, the medium can be provided in an artificial environment such as tissue engineering scaffold. Buffers such as phosphate-buffered saline may also serve as a suitable medium.

Release of protein may follow linear kinetics over a period of time. Such a release profile may be desirable to effect a particular dosing regimen. Certain embodiments of the invention provide systems for releasing proteins in a linear fashion over a period of at least 5, 10, or 14 days (see, for example, FIG. 4A). Certain embodiments of the invention provide systems allowing protein release over a period of at least 5, 10, 15, 20, 25, 30, or 34 days (see, for example, FIG. 5C).

Provided methods and systems allow release of functional proteins, such as discussed below in Example 8. In some embodiments, protein from thin films has at least 50%, 60%, 70%, 80%, and 90% activity (functional protein as compared to total protein) after being released from the films. In some embodiments, proteins released from thin films maintain up to as much 100% activity (see, for example, FIG. 7.)

EXAMPLES

Example 1

Construction of Decomposable Protein-Releasing Films

In this Example, decomposable protein-releasing films were constructed by layer-by-layer deposition onto glass or quartz substrates. Biological polyanions were used between layers of cationic polymers and layers of cationic protein, thus generating a tetralayer structure that was repeated to build the film.
Reagents and Solutions Linear poly(ethylenimine) (LPEI, Mn=25000) was obtained from Polysciences, Inc (Warrington, Pa.) and poly (sodium 4-styrenesulfonate) (PSS, Mn=1000000) was obtained from Sigma-Aldrich (St. Louis, Mo.). Chondroitin sulfate sodium salt (Mn=60000) was obtained from VWR Scientific (Edison, N.J.) and heparin sodium salt was obtained from Celsus Laboratories (Cincinnati, Ohio). Poly 1 was synthesized as previously described[15]. Poly 2 was synthesized in a manner similar to that used to synthesize Poly 1. Lysozyme and *Micrococcus lysodeikticus* bacteria were obtained from Sigma Aldrich (St. Louis, Mo.). All commercial polyelectrolytes were used as received without further purification. A Micro BCA Protein Assay Kit was obtained from Pierce (Rockford, Ill.) and used according to manufacturer instructions. Glass and quartz slides (substrates) were obtained from VWR Scientific (Edison, N.J.). Deionized water (18.2 MΩ, Milli-Q Ultrapure Water System, Millipore) was used for all washing steps. Dulbecco's PBS buffer was prepared from 10× concentrate available from Invitrogen (Frederick, Md.).
Preparation of Polyelectrolyte Solutions LPEI and PSS were dissolved in deionized water to a concentration of 10 mM with respect to repeat unit and pH adjusted to 4.25 and 4.75 respectively. Heparin, chondroitin, Poly 1, and Poly 2 were prepared in sodium acetate buffer (pH 5.1, 100 mM) at a concentration of 2 mg/mL. Lysozyme was prepared at a concentration of 0.5 mg/mL in 100 mM sodium acetate buffer, pH 5.1.
Film Construction Glass substrates or quartz slides (1"×¼") were rinsed with methanol and deionized water, dried under a stream of dry nitrogen, and plasma-etched in oxygen using a Harrick PDC-32G plasma cleaner on high RF power for 5 minutes. Ten base layers of (LPEI/PSS) were deposited upon plasma-etched substrates with a Carl Zeiss HSM series programmable slide stainer according to the following protocol: 5 minutes of dipping in LPEI, followed by three washes (10, 20, and 30 s each) in deionized water, followed by 5 minutes in PSS and three deionized water washes (10, 20 and 30 s each) for 10 repetitions. On top of the base layers, tetralayers incorporating lysozyme were built with the following architecture: (Poly 1/heparin/lysozyme/heparin)$_n$, where n refers to the number of tetralayers deposited on the substrate. A typical dipping protocol would be 10 minutes in a solution of Poly 1, 3 washes (10, 20, and 30 s each), 7.5 minutes in heparin with 3 washes (10, 20, and 30 s each), 10 minutes in the protein with 2 washes (20 and 30 s each) and 7.5 minutes in heparin with 3 washes (10, 20, and 30 s each). For the films characterized and used in Examples 2-6, Poly1 was dissolved in 100 mM sodium acetate buffer, pH 5.1. The protein used in the present Example (lysozyme) and the polyanion (heparin) were similarly dissolved in 100 mM sodium acetate buffer, pH 5.1. In the present Example, films were controlled to be approximately 0.75 inches×approximately 0.25 inches in size, or approximately 1.2 cm$^2$.

At the dipping conditions used (pH 5), Poly1 is cationic, and lysozyme was anticipated to be cationic as well (isoelectric point of 11). A four-layered repeat unit architecture with an anionic polymer (see FIG. 2) in between Poly1 and lysozyme was used, allowing deposition of layers of opposite charges adjacent to one another. Films were thus comprised of tetralayers having the structure (Poly1/heparin/lysozyme/heparin).

Example 2

Characterization of Protein-Releasing Films

In this Example, protein-releasing films constructed as described in Example 1 were characterized in terms of protein incorporation and growth.
Materials and Methods Varying numbers of tetralayers were deposited onto clean quartz substrates pre-treated with 10 base layers. Three techniques were used to analyze buildup. The thickness of the resulting films was measured by scoring the samples to the base of the film with a razor blade and measuring the step height using a profilometer (P10 Surface Profiler) with a 2 µm tip radius stylus. Protein incorporation in the film was measured by UV-Vis spectroscopy. A profile was taken of each sample on a Cary 6000i spectrophotometer from 200-800 nm. Proteins absorb at 280 nm due to tryptophan, tyrosine, and cysteine, and the intensity of absorption can then be correlated to protein buildup within the film. Absorbance values at 320 nm were measured as a baseline value and was subtracted from absorbance values at 280 nm. Baseline-corrected absorbance values were plotted against number of tetralayers.

To quantify the total protein concentration in the film, constructed films were spontaneously dissolved using 1 mL of 1M NaOH for 1 hour, which disrupts film architecture and releases all incorporated drug. A 50 µL sample was quenched in 1×PBS and read using a Micro BCA Protein Assay Kit (Pierce Biotechnology, Rockford, Ill.). Bicinchoninic acid can be used to quantify protein concentration by detecting a reduction of copper by the protein of interest in an alkaline environment. A color change can be monitored and compared to a constructed standard curve. Triplicate 100 µL aliquots of standards and samples were run in 96 well plates according to the manufacturer's protocol and read on a microplate reader (PowerWave XS, BioTek, Winooski Vt.).

Using measurements from standard samples of known concentration, a standard curve of concentration versus slope was constructed for the concentration range 0-200 µg/mL. The standard curve was linear over this concentration range. Lysozyme concentrations of unknown samples were interpolated from the standard curve using the slopes for each sample. The error bars in FIGS. 3-7 represent a 99% confidence interval calculated from triplicate repeat samples of 2 independent trials (resulting in a total of 6 data points for each sample or standard.

Results and Discussion

Film buildup was tracked by monitoring thickness, protein incorporation, and instantaneous protein release (see FIG. 3). After a brief induction period where little protein incorporation, film thickness, or protein release is achieved (approximately 10-20 tetralayers), all three methods indicate that the films build and incorporate protein in a roughly linear fashion (FIG. 3 A-D).

An induction period for multilayer growth is typical of many LbL systems and has been reported in the literature[23,24]. It is believed, without being held to theory, that in this initial period, surface effects influence the buildup of the LbL film until complete surface coverage is achieved after several adsorption cycles. Furthermore, superlinear growth occurs as interdiffusion occurs within the layers of the film.

Protein content was measured by two techniques (UV-Vis, FIG. 3A; BCA, FIG. 3C), and total film buildup was measured by profilometry as described above (see FIG. 3B). Protein incorporation became linear after approximately 10 tetralayers, whereas thickness increase became linear at approximately 20 to 30 tetralayers. The thickness per tetralayer repeat unit in the linear growth regime is approximately 0.42 µm (420 nm), which is large in comparison with typical electrostatic multilayer systems that exhibit 10 to 100 nm per bilayer pair.

The disparity between the kinetics of protein incorporation and that of thickness suggests that although protein incorporation is substantially linear after just 10 tetralayers, the polymer composition in the film may be changing in a nonlinear fashion during this initial period. This regime of superlinear growth is hypothesized to be due to intermolecular interdiffusion of macromolecules into the film during the adsorption process, which leads to increasingly thick films[24,25] until the linear growth phase is reached.

It is believed, without being held to theory, that the linear characteristics of the second growth phase is created by a "front" in which interdiffusion of polymers into the bulk film remains possible. Such a front may vastly increase the amount of drug that can be incorporated in each dip step compared to the amount of drug that can be incorporated during initial steps (when the film and therefore the front are thinner). It is believed, without being held to theory, that underneath the front is a "reorganized" layer that is impermeable to diffusion, retaining the linearity of the film[23-25]. The diffusive character of the front and therefore of the film are affected by a number of factors including hydrophilicity of the polymer backbone, charge density of the polyions, and molecular weight of the polymers involved.

In general, there is strong agreement between the three measurement techniques, indicating excellent protein incorporation in the films, with linear build-up after an initial induction period (see FIG. 3D). This linearity makes it simple to predict the additional amount of protein incorporated by adding subsequent tetralayers, as the amount incorporated increases linearly with the additional number of tetralayers dipped. For [Poly1/heparin/lysozyme/heparin]$_{80}$ films, a UV-Vis signal of 2.064 units at 280 nm (FIG. 1A) corresponded with a profilometry thickness of 23.7 µm (23780 nm) (FIG. 1B), or approximately 1365 µg of loaded lysozyme.

Example 3

Characterization of Protein Release from Films

In this Example, total protein released from films was determined as a function of time.

Materials and Methods

Samples were released into phosphate buffered saline (pH 7.4) at either room temperature or 37 degrees Celsius in a microcentrifuge tube containing 1 mL of PBS. At a series of different time points, 0.5 mL of sample was removed and 0.5 mL of fresh PBS was introduced to the sample container. Samples were frozen at −20° C. until analyzed. Release of lysozyme into the solution was detected using the Micro BCA Protein Assay Kit as described in Example 2. For each time point analyzed, the total amount of protein released up to the time point was measured.

Results and Discussion

Proteins were released from films at 37° C. in PBS to approximate physiologic conditions and analyzed using a Micro BCA kit. As shown in FIG. 4A (which depicts a release curve for 43 tetralayer-films), lysozyme is released with a linear trend over a period of approximately 14 days. Approximately 780 µg of incorporated protein (or 650 µg/cm$^2$) was released over the approximately 14-day time period.

The linear release trend may be desirable from multiple perspectives. This release trend may desirable for the drug delivery applications, because it allows constant, low levels of protein to be released from the surface. In burst release profiles, most of the protein is released instantly, consequently lost to a greater body volume, and cleared before therapeutic action can take place. In such burst release profiles, only a minority of drug is controlled in release. In contrast with burst release profiles, nearly all of the release from protein-releasing films of the invention occurs in a controlled, easy to predict (and therefore dose-oriented) fashion based on numbers of tetralayers used to build the film. Controlled delivery has significant advantages over pill or bolus injection methods, as it allows the concentration of the protein at the local site of interest to be kept within a therapeutic window between an upper limit of toxicity and a lower limit of effectiveness. In some embodiments, the invention therefore provides a new modality for the timed local release of proteins within the body where the expense or size of a dose was previously prohibitive. Loading more drug is possible by increasing the number of tetralayers in the film; it is also possible to predict the additional amount of protein incorporated.

In addition to these advantages, the controlled and linear release profile suggests a surface erosion mechanism for release. Previous studies of the degradation of poly(β-aminoester)-based LbL delivery indicated that degradation indeed occurs by surface-based erosion, based on AFM and similar measurements. The experiments described in this Example also illustrate that very large amounts of protein can be incorporated even in a mid-range number of tetralayers (films from 10 to 80 tetralayers were examined). Protein incorporation of up to approximately 1365 µg (or 1.14 mg/cm$^2$) is possible at 80 tetralayers in this particular Example (see FIG. 3C). Most growth factor applications, by comparison, require only nanogram/mL concentrations of protein, suggesting that these films have a high upper limit loading capacity for such applications.

Example 4

Tuning of Total Dose and Time Scale of Release by Modifying the Number of Multilayer Units It can be envisioned that by tuning the number of tetralayers used in this system, it would be possible to change both the total dose administered as well as the time scale of release. FIG. 4B depicts a family of release curves for films with (Poly 1/heparin/lysozyme/heparin)$_n$ architecture and varying numbers of tetralayers. As can be observed from FIG. 4B, with increasing numbers of tetralayers, both the total amount of drug released and the time span of release are increased, consistent with the hypothesized mechanism of surface erosion. Films with 20 tetralayers released 100 µg of protein over 7 days, while films with 43 tetralayers released 780 µg of protein over 14 days. Bulk releasing films would possibly have increased loading with increasing numbers of tetralayers, but would release the entire load over the same amount of time, independent of the number of tetralayers. This characteristic of bulk releasing films, when taken together with the linear buildup and release of the film, supports the idea that a surface erosion mechanism of release (rather than a bulk diffusion mechanism) is responsible, as demonstrated and discussed in previous publications[2,19].

Release studies also allowed for the calculation of the fraction of loaded films that is actually released. To address this question, two sets of films were constructed with the architecture (Poly1/heparin/lysozyme/heparin) and varying numbers of tetralayers. One set of films was released at 37° C. and the other was instantaneously released using a rapid deconstruction of the film, as described in the Materials and Methods section of Example 3. The total release was calculated in each instance, and plotted in FIG. 4C. Nearly 95% release or higher is observed at low numbers of tetralayers (50 tetralayers and below). At 80 tetralayers, approximately 85% release is achieved. Because this is a fully degradable system, it is anticipated that eventual recovery of the remaining 15% would occur over more extended time periods. Without being held to theory, it is hypothesized that the thickness of the film and incomplete degradation of overlying polymer networks hinders further release of protein from the film.

Example 5

Tuning of Total Dose and Time Scale of Release by Modifying the Molecular Structure of the Polymer One of advantage of using a synthetic erodible polymer is that the drug delivery from the device can be tuned through additional mechanisms over those already discussed by modifying the molecular structure of the polymer used. Poly1 is only one of a large family of poly(β-aminoesters) that can be used in these films; by tuning the composition of the polymers used for this purpose, one can alter the degradability of the ester bond and therefore decrease or increase the time scale over which the film degrades.

A second poly(β-aminoester), Poly2, was used to explore the effect of the kinetics of ester hydrolysis on drug release from the constructed multilayers (see FIG. 1). Poly2 differs from Poly1 in that it has an additional two methylene units in the backbone next to the ester bond, making Poly2 more hydrophobic and making the ester bond less susceptible to hydrolysis. This decreased susceptibility to hydrolysis is predicted to decrease degradation and therefore increase time span of release. Thus, characterization and comparison between Poly1 and Poly2 films yields further interesting information on the erosion of these films as well as demonstrating that one can to tune release by tuning the characteristics of the synthetic polymer used.

Comparing buildup data of Poly2 compared to similar films for Poly1 (FIG. 5A), there is similar agreement between the three measurement techniques, suggesting that linear film buildup and incorporation are first observed at 20 tetralayers. As an illustrative example, the profilometry data for P1 and P2 films have been plotted in FIG. 5B to show the relative film buildup between the two compositions (100% in FIG. 5A corresponds 50 tetralayer values: a UV-Vis reading of 1.52 absorbance units at 280 nm, a film thickness of approximately 13.23 µm, and protein incorporation of approximately 960 µg). In FIG. 5B, a representative comparison of profilometry measurements show that while both films exhibit similar growth trends, Poly2 incorporates more material at each measurement point. For example, at 50 tetralayers, Poly1 is able to incorporate approximately 780 µg of protein, whereas Poly2 is able to incorporate about 960 µg of protein.

The phenomenon of increasing drug loading with increasing hydrophobicity is well understood. It is believed, without being held to theory, that increasing hydrophobicity leads to a more "loopy" film architecture in which there are longer segments of polymer between electrostatic connections with the growing film and new polymer chains being incorporated. This increases both the film thickness and its ability to load more drug (by having a greater volume in which to pack drug). Hydrophobic interactions between the drug and the polymer may further enhance drug loading in these systems.

Figure 5C:
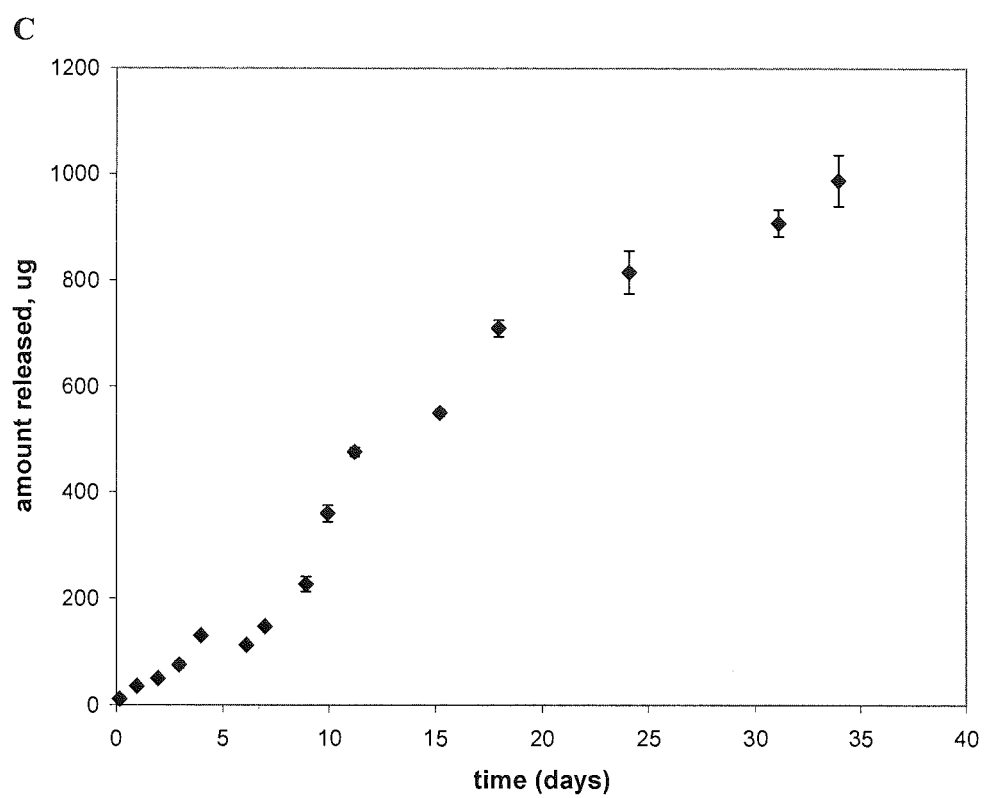

FIG. 5C depicts amount of protein released over time from a film with the architecture (Poly2/heparin/lysozyme/heparin)$_n$. Over 34 days of release are observed with Poly2 films, indicating a 2× increase in release time using the more hydrophobic polymer. These results demonstrate that the time period of release can be modified by tuning the degradable polymer used. This data further supports the idea that surface erosion is the likely mechanism of release, as it is the hampered erosion of the ester bond that leads to increased release times.

Example 6

Tuning of Total Dose and Time Scale of Release by Using a Different Polyanion

Release behavior of the films can also be modified by incorporating a different polyanion, such as chondroitin. Chondroitin sulfate was incorporated in films of the architecture [Poly1/chondroitin/lysozyme/chondroitin] and varying numbers of tetralayers. Profilometry, UV-vis and instantaneous release curves are plotted and depicted in FIG. 6A. Contrary to the film growth behavior for heparin, chondroitin buildup is characterized by a more extended period of time in the first, superlinear regime of the buildup process enabled by interdiffusion. Even by 50 tetralayers, it is unclear whether the films are beginning to build linearly or not; it is perhaps at this point that the films are just entering the second, linear regime of interdiffusion-based multilayer assembly. Film thickness values at 50 tetralayers are much lower than those of Poly 1/heparin or Poly 2/heparin films, suggesting that interdiffusion in these films may not be as extensive as that in films built with heparin. Without being held to theory, less extensive interdiffusion may explain the more extended period before entering the linear interdiffusion/permeation controlled regime observed for chondroitin-containing films as compared to heparin-containing films. Protein incorporation is also lower than that of comparable heparin-based films. Table 1 summarizes UV-Vis absorbance at 280 nm (indicative of protein incorporated), thickness, and instantaneous protein release values for varying film constructions.

TABLE 1

Protein incorporation and thickness for films of varying constructions

| Film construction | UV-Vis absorbance | Thickness (μm) | Protein instantaneously released (μg) |
|---|---|---|---|
| (Poly1/chondroitin/lysozyme/chondroitin)$_{50}$ | 0.24 | 2.73 | 160 |
| (Poly1/heparin/lysozyme/heparin)$_{50}$ | 1.24 | 7.90 | 780 |
| (Poly2/heparin/lysozyme/heparin)$_{50}$ | 1.52 | 13.23 | 960 |

Figure 6A:
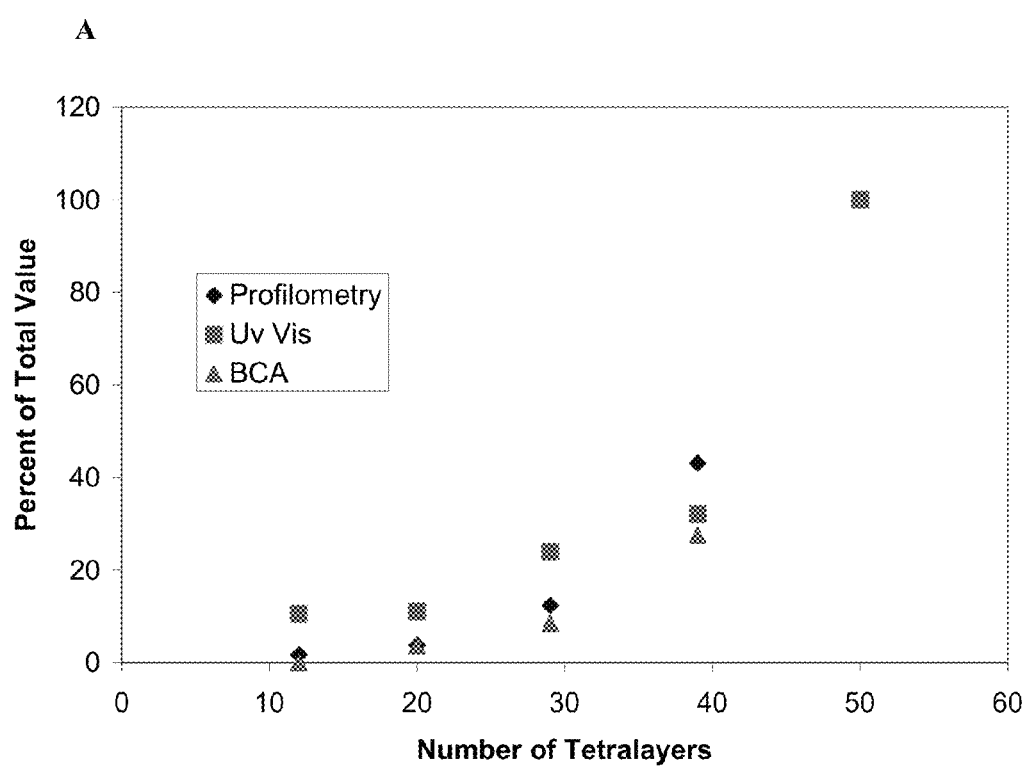
FIG. 6A-C shows results of characterization studies of chondroitin-containing films. (A): The number of (Poly1/chondroitin/lysozyme/chondroitin) tetralayers is plotted against the signal recorded at that point of construction. Each signal value is taken as a percentage of the signal at 50 tetralayers. (B): Release curves of chondroitin-containing and heparin-containing films. (C): Release curves of films comprising various numbers of tetralayers constructed with lysozyme and chondroitin.
Figure 6B:
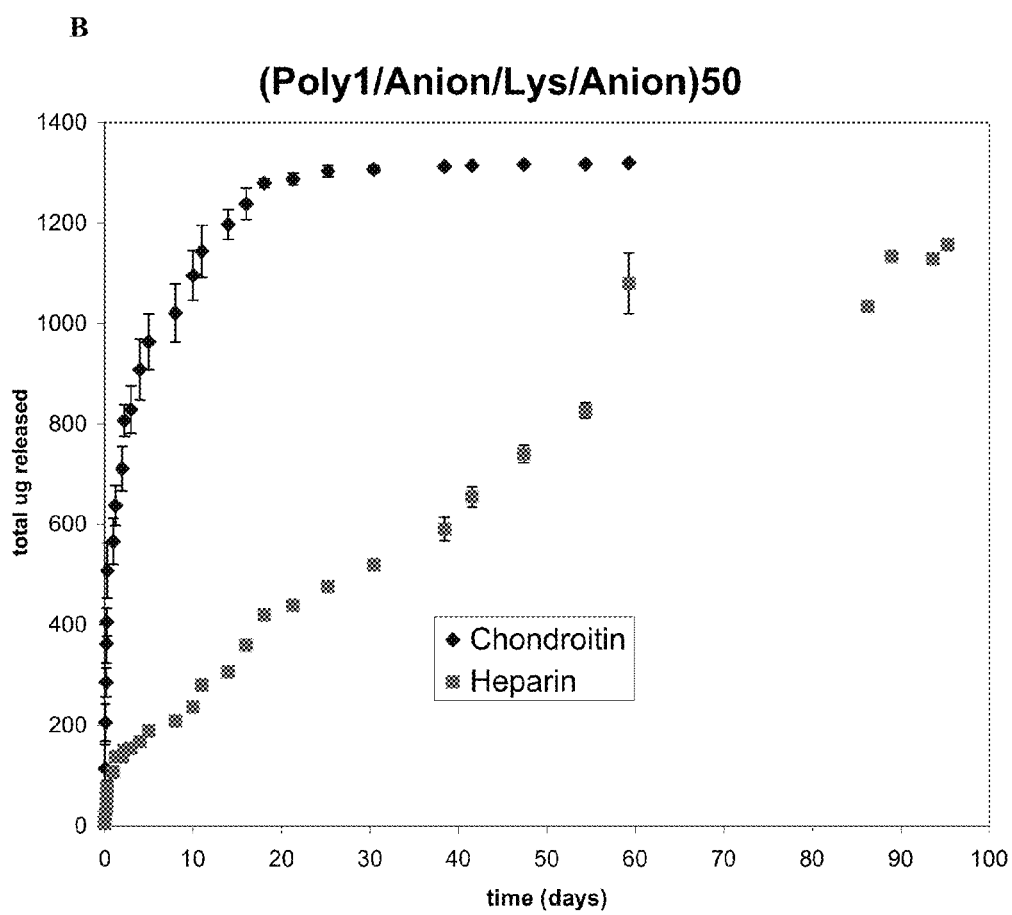
Figure 6C:
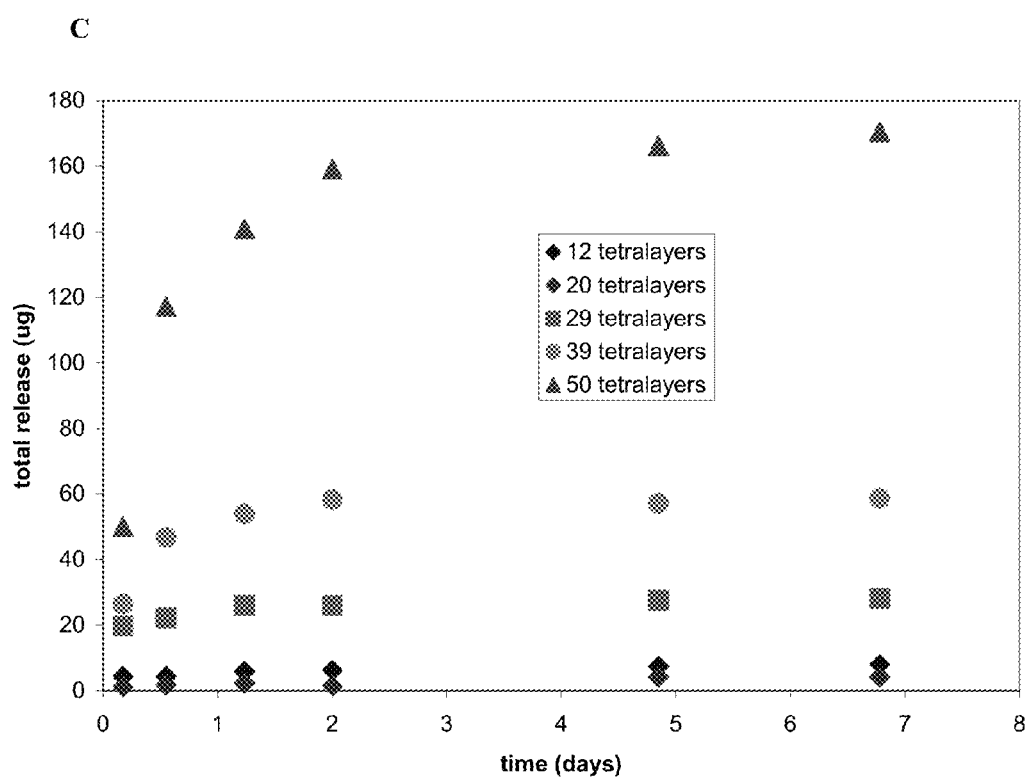

Whereas linear incorporation was observed for heparin-containing films, superlinear incorporation was observed for chondroitin-containing films. Chondroitin-containing films showed an inverse exponential pattern of release, exhibiting a power law dependence with more lysozyme released first from the lysozyme-rich top layers of the film (see FIG. 6B). The lower incorporation of lysozyme and faster time to completion of release of 3 to 4 days (see FIGS. 6B and 6C) are consistent with the overall thinner film and lower loading of protein. These films may be useful in applications in which a fairly sustainable burst at the beginning is desirable, with low levels of sustained release following. Shown in FIG. 6C are release curves for chondroitin-containing films comprised of varying numbers of tetralayers. With increasing numbers of tetralayers, a trend of increased loading and time to complete release was observed, as had been seen with Poly1/heparin and Poly2/heparin films. The results in FIG. 6B also show that total dose and release kinetics of chondroitin-containing films can be tuned.

Example 7

Activity of Protein Released from Films

One concern in encapsulating proteins for drug delivery is whether the processing conditions will destroy the activity of the encapsulated component. To quantify the functionality of released enzyme, activity assays of lysozyme were performed. Lysozyme's native activity is to cleave bacterial cell walls; one can detect the amount of functional lysozyme in solution by a kinetic reduction in turbidity of a bacterial solution.

Materials and Methods

Lysing of bacteria, such as can be achieved by lysozyme, will clear a cloudy suspension of bacteria; this clearing can be measured as a decrease in absorbance at 450 nm. Measurement was done as a kinetic plate reading assay. When absorbance at 450 nm is plotted against time, the slope of the graph is proportional to the concentration of lysozyme present in the solution.

Using measurements from standard samples of known concentration, a standard curve of concentration versus slope was constructed for the concentration range 0-200 μg/mL. The standard curve was linear over this concentration range. Functional lysozyme concentrations of unknown samples were interpolated from the standard curve using the slopes for each sample. In these tests, 290 μL of a 0.25 mg/mL solution of *Micrococcus lysodeikticus* was mixed with 10 μL of sample or standard. Each sample or standard was prepared in triplicate. Samples and standards were read in a 96 well plate at 450 nm every 15 seconds for a total of 10 readings. The readout from the assay is a concentration of lysozyme present based on the lysing ability of the sample, and thus represents the concentration of functional protein present in the sample.

Results and Discussion

Figure 7:
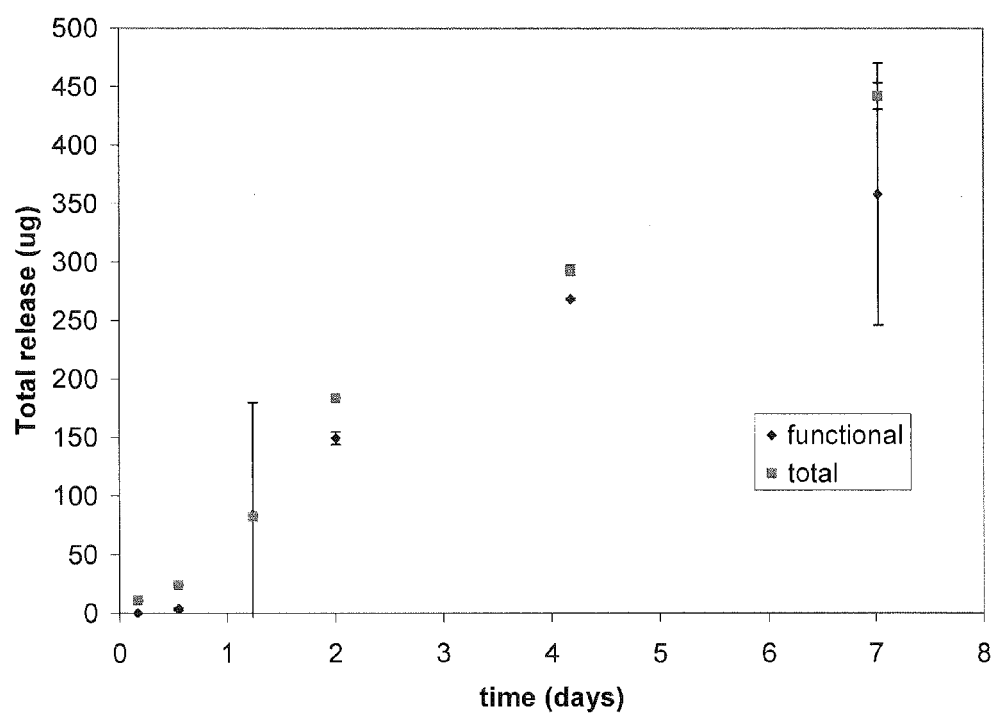
FIG. 7 shows results of assays to determine function of released protein. The total amount of protein detected using the Micro BCA Protein Kit (Piece Biotechnologies) was plotted with the total amount of functional protein detected using the kinetic functional lysozyme assay; both values were plotted versus time.

In FIG. 7, results of the micro-BCA assay for typical films are plotted in tandem with the results of a functional assay that reports the concentration of active enzyme present in a given sample. 80%-100% of activity is preserved within the films throughout the length of the trial. These rates of activity compare favorably with those of protein release from LbL films in the literature. In films described by Derbal et al.[26], activity at physiologic pH was possible, but long term activity of the enzyme (over a period of months) dropped to levels of approximately 30% of their original value. In capsules described by Caruso et al. and Tiourina et al.[9,10], excellent retention of activity was possible, ranging from 70 to 100%; however, the capsules required a high pH to release, which is unattainable for many medical device release applications, and the system exhibited a burst style of release.

By combining hydrolytic degradability in a polyion directly with the protein of choice in LbL assembly, it is possible to protect and retain protein for long periods of time while sustaining the ability for extended release at biologically relevant conditions.

Example 8

Effect of Dipping Temperature on Incorporated Protein

Figure 8:
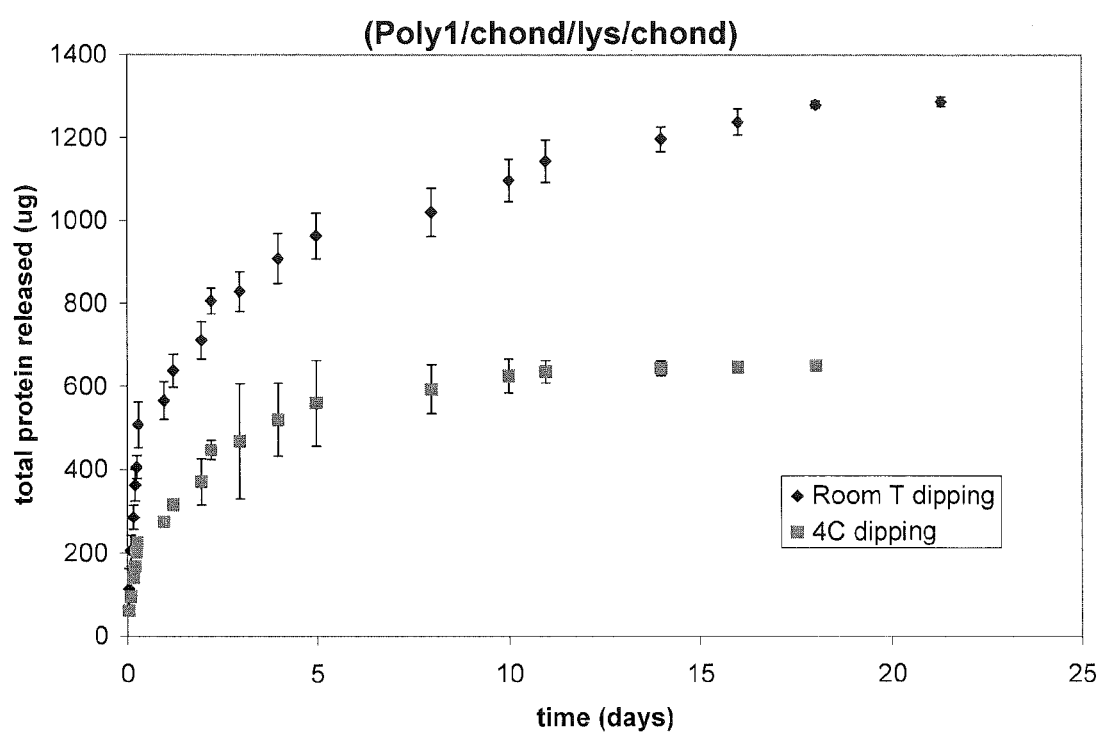
FIG. 8 shows effects of dipping temperature on protein incorporation. The dipping process was performed in a cold room at about 4° C., and an identical experiment was performed at room temperature. Both experiments were released at room temperature to show the effect of dipping temperature on the amount of protein incorporated.

Due to the fragile nature of many of the proteins that could potentially be used as drugs with films and methods of the present invention, the possibility of dipping at a reduced temperature in order to enhance protein stability during incorporation was explored. To lower the temperature of the dipping baths during the dipping process, the dipping apparatus was placed at 4° C. and the experiment run in a similar fashion to that of room temperature. As can be seen from FIG. 8, the amount of incorporated protein decreases with decreased with dipping temperature but retains the general trends and characteristics during release of films dipped at room temperature.

Although lower amounts of protein are incorporated when dipping was performed at lower temperatures, lower dipping temperatures may be desirable in some embodiments, particularly with heat-sensitive proteins. Higher amounts of protein may be achieved with lower dipping temperatures by, for example, increasing the number of multilayers in the film and/or the concentration of protein in the adsorption baths.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

Other Embodiments and Equivalents

While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments of the invention, it is to be understood that the invention is not restricted to those particular embodiments. Rather, the invention includes all embodiments that are functional and/or equivalents of the specific embodiments and features that have been described and illustrated.

REFERENCES

1. Decher, G. Fuzzy nanoassemblies: Toward layered polymeric multicomposites. *Science* 277, 1232-1237 (1997).
2. Vazquez, E., Dewitt, D. M., Hammond, P. T. & Lynn, D. M. Construction of hydrolytically-degradable thin films via layer-by-layer deposition of degradable polyelectrolytes. *Journal of the American Chemical Society* 124, 13992-13993 (2002).
3. Decher, G., Eckle, M., Schmitt, J. & Struth, B. Layer-by-layer assembled multicomposite films. *Current Opinion in Colloid & Interface Science* 3, 32-39 (1998).
4. Hammond, P. T. Form and function in multilayer assembly: New applications at the nanoscale. *Advanced Materials* 16, 1271-1293 (2004).
5. Fu, K., Pack, D. W., Klibanov, A. M. & Langer, R. Visual evidence of acidic environment within degrading poly(lactic-co-glycolic acid) (PLGA) microspheres. *Pharmaceutical Research* 17, 100-106 (2000).
6. Berg, M. C., Yang, S. Y., Hammond, P. T. & Rubner, M. F. Controlling mammalian cell interactions on patterned polyelectrolyte multilayer surfaces. *Langmuir* 20, 1362-1368 (2004).
7. Chung, A. J. & Rubner, M. F. Methods of loading and releasing low molecular weight cationic molecules in weak polyelectrolyte multilayer films. *Langmuir* 18, 1176-1183 (2002).
8. Berg, M. C., Zhai, L., Cohen, R. E. & Rubner, M. F. Controlled drug release from porous polyelectrolyte multilayers. *Biomacromolecules* 7, 357-364 (2006).
9. Caruso, F., Trau, D., Mohwald, H. & Renneberg, R. Enzyme encapsulation in layer-by-layer engineered polymer multilayer capsules. *Langmuir* 16, 1485-1488 (2000).
10. Tiourina, O. P. & Sukhorukov, G. B. Multilayer alginate/protamine microsized capsules: encapsulation of alpha-chymotrypsin and controlled release study. *International Journal of Pharmaceutics* 242, 155-161 (2002).
11. Etienne, O. et al. Degradability of polysaccharides multilayer films in the oral environment: an in vitro and in vivo study. *Biomacromolecules* 6, 726-733 (2005).
12. Picart, C. et al. Controlled degradability of polysaccharide multilayer films in vitro and in vivo. *Advanced Functional Materials* 15, 1771-1780 (2005).
13. Benkirane-Jessel, N. et al. Short-time timing of the biological activity of functionalized polyelectrolyte multilayers. *Advanced Functional Materials* 15, 648-654 (2005).
14. Lynn, D. M. & Langer, R. Degradable poly(beta-amino esters): Synthesis, characterization, and self-assembly with plasmid DNA. *Journal of the American Chemical Society* 122, 10761-10768 (2000).
15. Lynn, D. M., Langer, R. Degradable poly(beta-amino esters): synthesis, characterization, and self-assembly with plasmid DNA. *Journal of the American Chemical Society* 122, 10761-10768 (2000).
16. Akinc, A., Anderson, D. G., Lynn, D. M. & Langer, R. Synthesis of poly(beta-amino ester)s optimized for highly effective gene delivery. *Bioconjugate Chemistry* 14, 979-988 (2003).
17. Little, S. R. et al. Poly-beta amino ester-containing microparticles enhance the activity of nonviral genetic vaccines. *Proceedings of the National Academy of Sciences of the United States of America* 101, 9534-9539 (2004).
18. Wood, K. C., Chuang, Helen F., Batten, Robert D., Lynn, David M., Hammond, Paula T. Controlling interlayer diffusion to achieve sustained, multiagent delivery from layer-by-layer thin films. *PNAS* 103, 10207-10212 (2006).
19. Wood, K. C., Boedicker, J. Q., Lynn, D. M. & Hammond, P. T. Tunable drug release from hydrolytically degradable layer-by-layer thin films. *Langmuir* 21, 1603-9 (2005).
20. Jewell, C. M., Zhang, J., Fredin, N.J. & Lynn, D. M. Multilayered polyelectrolyte films promote the direct and localized delivery of DNA to cells. *J Control Release* 106, 214-23 (2005).
21. Jessel, N. et al. Multiple and time-scheduled in situ DNA delivery mediated by beta-cyclodextrin embedded in a polyelectrolyte multilayer. *Proceedings of the National Academy of Sciences of the United States of America* 103, 8618-8621 (2006).
22. Puleo, D. A., Kissling, R. A. & Sheu, M. S. A technique to immobilize bioactive proteins, including bone morphogenetic protein-4 (BMP-4), on titanium alloy. *Biomaterials* 23, 2079-2087 (2002).
23. Porcel, C. et al. Influence of the polyelectrolyte molecular weight on exponentially growing multilayer films in the linear regime. *Langmuir* 23, 1898-1904 (2007).
24. Porcel, C. et al. From exponential to linear growth in polyelectrolyte multilayers. *Langmuir* 22, 4376-4383 (2006).
25. Jourdainne, L. et al. Multiple strata of exponentially growing polyelectrolyte multilayer films. *Macromolecules* 40, 316-321 (2007).
26. Derbal, L., Lesot, H., Voegel, J. C. & Ball, V. Incorporation of alkaline phosphatase into layer-by-layer polyelectrolyte films on the surface of Affi-gel heparin beads:

Physicochemical characterization and evaluation of the enzyme stability. *Biomacromolecules* 4, 1255-1263 (2003).

We claim:

1. A decomposable thin film comprising at least one tetralayer unit, the tetralayer unit comprising:
    a degradable polyelectrolyte layer having a first electrostatic charge;
    a first polysaccharide layer disposed next to the degradable polyelectrolyte layer, the polysaccharide layer having a second electrostatic charge, the first and second electrostatic charges being opposite;
    a carrier layer disposed next to the first polysaccharide layer, the carrier layer including at least one growth factor; and
    a second polysaccharide layer disposed next to the carrier layer.

2. The decomposable thin film of claim 1, wherein the at least one growth factor is a vascular endothelial growth factor (VEGF), a bone morphogenic protein 2 (BMP-2), a bone morphogenic protein 4 (BMP-4), or a basic fibroblast growth factor (bFGF).

3. The decomposable thin film of claim 1, wherein the degradable polyelectrolyte is a hydrolysable polyelectrolyte.

4. The decomposable thin film of claim 1, wherein the carrier layer has a third electrostatic charge and the second polysaccharide layer has a fourth electrostatic charge, and wherein the first, the second, the third, and the fourth electrostatic charges are alternating anionic and cationic charges.

5. The decomposable thin film of claim 1, wherein the carrier layer consists of a protein.

6. The decomposable thin film of claim 1, wherein the degradable polyelectrolyte layer includes a polyelectrolyte selected from the group consisting of a synthetic polyelectrolyte, a natural polyelectrolyte, and a hybrid of a synthetic and a natural polyelectrolyte.

7. The decomposable thin film of claim 1, wherein the degradable polyelectrolyte layer includes one or more polyelectrolytes selected from the group consisting of a polyester, a polyanhydride, a polyorthoester, a polyphosphazene, and a polyphosphoester.

8. The decomposable thin film of claim 1, wherein the degradable polyelectrolyte layer is a polymer that includes one or more polyesters selected from the group consisting of a poly(β-amino ester), a poly(L-lactide-co-L-lysine), a poly(serine ester), a poly(4-hydroxy-L-proline ester), and a poly[α-(4-aminobutyl)-L-glycolic acid].

9. The decomposable thin film of claim 1, wherein the degradable polyelectrolyte layer is a poly(β-amino ester) that includes a repeating unit represented by a structural formula selected from the group consisting of

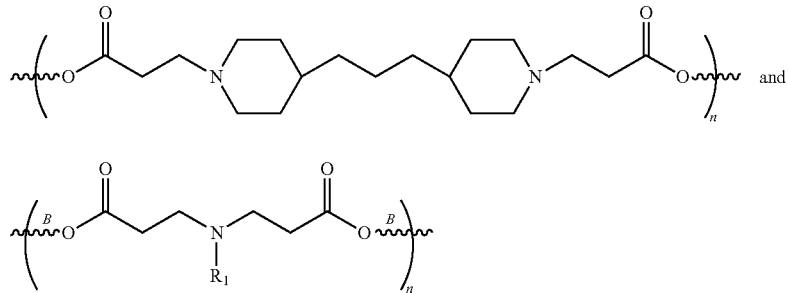

wherein:
each linker B is independently a carbon chain of 1 to 30 carbon atoms or a heteroatom-containing carbon chain of 1 to 30 atoms, each of which is optionally substituted with at least one group selected from a branched or unbranched alkyl, a branched or unbranched alkenyl, a branched or unbranched alkynyl, an amino, an alkylamino, a dialkylamino, a trialkylamino, an aryl, a ureido, a heterocyclic, an aromatic heterocyclic, a cyclic, an aromatic cyclic, a halogen, hydroxyl, an alkoxy, a cyano, an amide, a carbamoyl, a carboxylic acid, an ester, a carbonyl, a carbonyldioxyl, an alkylthioether, or a thiol group;

each $R_1$ is independently hydrogen, a branched and unbranched alkyl, a branched or unbranched alkenyl, a branched or unbranched alkynyl, an aryl, a halogen, a hydroxyl, an alkoxy, a carbamoyl, a carboxyl ester, a carbonyldioxyl, an amide, a thiohydroxyl, an alkylthioether, an amino, an alkylamino, a dialkylamino, a trialkylamino, a cyano, a ureido, a substituted alkanoyl, a cyclic, a cyclic aromatic, a heterocyclic, and an aromatic heterocyclic group, each of which is further optionally substituted with at least one substituent selected from the group consisting of a branched or unbranched alkyl, a branched or unbranched alkenyl, a branched or unbranched alkynyl, an amino, an alkylamino, a dialkylamino, a trialkylamino, an aryl, a ureido, a heterocyclic, an aromatic heterocyclic, a cyclic, an aromatic cyclic, a halogen, a hydroxyl, an alkoxy, a cyano, an amide, a carbamoyl, a carboxylic acid, an ester, a carbonyl, a carbonyldioxyl, an alkylthioether, and a thiol group; and n is an integer greater than or equal to 5.

10. The decomposable thin film of claim 9, wherein the repeating unit is represented by the following structural formula

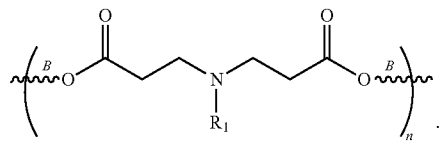

11. The decomposable thin film of claim 9, wherein the repeating unit is represented by the following structural formula

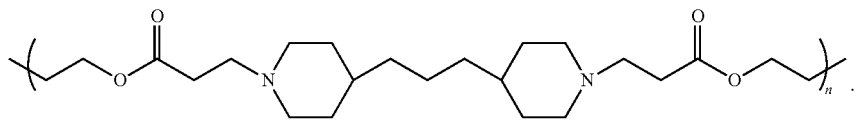

12. The decomposable thin film of claim 9, wherein the repeating unit is represented by the following structural formula

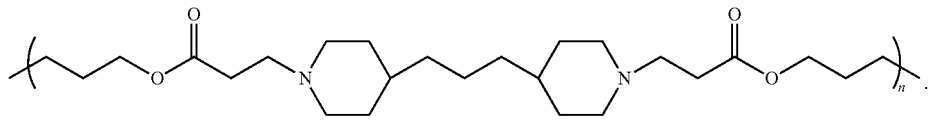

13. The decomposable thin film of claim 1, wherein the degradable polyelectrolyte layer is a polymer that includes one or more of a poly(styrene sulfonate), a poly(acrylic acid), a linear poly(ethylene imine), a poly(diallyl dimethyl ammonium chloride), and a poly(allylamine hydrochloride).

14. The decomposable thin film of claim 1, wherein the degradable polyelectrolyte is a hydrolysable polyelectrolyte, a thermal degradable polyelectrolyte, an enzymatically degradable polyelectrolyte, or photolyticaly degradable polyelectrolyte.

15. The decomposable thin film of claim 1, wherein the degradable polyelectrolyte includes a biodegradable polymer.

16. The decomposable thin film of claim 15, wherein the biodegradable polymer includes one of more polymer selected from a polyhydroxyacid, a polypropylfumerate, a polycaprolactone, a polyamide, a poly(amino acid), a polyacetal, a polyether, a polycyanoacrylate, a polyurethane, and a polysaccharide.

17. The decomposable thin film of claim 1, wherein the decomposable thin film is a hollow shell.

18. A device comprising a substrate and the decomposable thin film of claim 1, wherein the decomposable thin film is disposed on the substrate.

19. The device of claim 18, wherein the substrate is nonplanar.

20. The device of claim 18, wherein the substrate is a particle, a tube, a sphere, a strand, a coiled strand, or a capillary network.

21. The device of claim 18, wherein the substrate is hydrolytically degradable.

22. The device of claim 18, wherein the substrate includes a bioactive agent.

23. The device of claim 18, wherein the substrate includes at least one material selected from a metal, a metal oxide, a plastic, a ceramic, a silicon, a glass, a mica, a graphite, a hydrogel.

24. The decomposable thin film of claim 1, wherein the first polysaccharide layer includes a first polysaccharide, the second polysaccharide layer includes a second polysaccharide, and wherein the first and the second polysaccharides are the same.

25. The decomposable thin film of claim 1, wherein the first polysaccharide layer and the second polysaccharide layer each includes a polysaccharide independently selected from the group consisting of heparin sulfate, chondroitin sulfate, hyaluronic acid, and dextran sulfate.

26. The decomposable thin film of claim 1, wherein the decomposable thin film comprises at least 10 tetralayer units.

27. The decomposable thin film of claim 26, wherein the decomposable thin film comprises at least N tetralayer units, wherein N is an integer selected from 20, 30, 40, 50, 60 70, and 80.

28. A method of releasing a protein, comprising the steps of:
   providing a decomposable thin film of claim 1; and
   placing the decomposable thin film in a medium, thereby causing the release of the at least one growth factor.

29. The method of claim 28, wherein the release of the at least one growth factor exhibits linear kinetics over a period of at least M days, wherein M is an integer selected from 5, 10, and 14.

30. The method of claim 28, wherein the release of the at least one growth factor continues over a period of at least K days, wherein K is an integer selected from 5, 10, 15, 20, 25, 30, and 34.

31. The method of claim 28, wherein the at least one growth factor retains at least P % activity after the release, wherein P is an integer selected from 50, 60, 70, 80, and 90.

* * * * *